US005686582A

United States Patent [19]

Greve et al.

[11] Patent Number: 5,686,582
[45] Date of Patent: Nov. 11, 1997

[54] MULTIMERIC FORMS OF HUMAN RHINOVIRUS RECEPTOR PROTEIN

[75] Inventors: Jeffrey M. Greve, Woodbridge; Alan McClelland, Old Saybrook, both of Conn.

[73] Assignee: Bayer Corporation, West Haven, Conn.

[21] Appl. No.: 464,083

[22] Filed: Jun. 5, 1995

Related U.S. Application Data

[63] Continuation of Ser. No. 318,038, Oct. 4, 1994, which is a continuation of Ser. No. 171,261, Dec. 21, 1993, abandoned, which is a continuation of Ser. No. 977,590, Nov. 17, 1992, abandoned, which is a continuation of Ser. No. 704,984, May 24, 1991, abandoned, which is a continuation-in-part of Ser. No. 556,238, Jul. 20, 1990, abandoned.

[51] Int. Cl.$^6$ .................. C07K 14/705; A61K 38/00
[52] U.S. Cl. .................. 530/402; 530/395; 530/403; 424/185.1; 424/193.1; 424/194.1
[58] Field of Search .................. 530/350, 395, 530/402, 403; 424/185.1, 193.1, 194.1

[56] References Cited

U.S. PATENT DOCUMENTS

| | | | |
|---|---|---|---|
| 4,171,365 | 10/1979 | Diana et al. | 424/273 |
| 4,209,526 | 6/1980 | Diana et al. | 424/273 |
| 4,232,161 | 11/1980 | Diana et al. | 546/279 |
| 4,234,725 | 11/1980 | Diana et al. | 544/140 |
| 4,261,928 | 4/1981 | Diana et al. | 568/331 |
| 4,372,976 | 2/1983 | Diana | 424/331 |
| 4,427,653 | 1/1984 | Springer | 424/85 |
| 4,451,476 | 5/1984 | Diana | 424/272 |
| 4,843,087 | 6/1989 | Diana | 514/374 |
| 4,956,281 | 9/1990 | Wallner et al. | 435/69.3 |
| 5,109,123 | 4/1992 | Reinherz et al. | 536/27 |
| 5,235,049 | 8/1993 | McClelland et al. | 435/240.2 |
| 5,284,931 | 2/1994 | Springer et al. | 424/85.8 |

FOREIGN PATENT DOCUMENTS

| | | | |
|---|---|---|---|
| A-14630/88 | 10/1988 | Australia | C07K 15/12 |
| B-48767/90 | 2/1990 | Australia | C07K 13/00 |
| 0169146A3 | 1/1986 | European Pat. Off. | C12N 15/00 |
| 0169729A2 | 1/1986 | European Pat. Off. | G01N 33/577 |
| 0192175A2 | 8/1986 | European Pat. Off. | C12N 5/00 |
| 0207453A2 | 1/1987 | European Pat. Off. | C07D 413/12 |
| 0227604A2 | 7/1987 | European Pat. Off. | C07K 7/08 |
| 0261403A2 | 3/1988 | European Pat. Off. | C12N 15/00 |
| 0280578A2 | 8/1988 | European Pat. Off. | C07K 3/20 |
| 0287076B1 | 10/1988 | European Pat. Off. | C12P 21/00 |
| 0289949A2 | 11/1988 | European Pat. Off. | C12N 15/00 |
| 0314863A2 | 5/1989 | European Pat. Off. | A61K 37/02 |
| 0319815A2 | 6/1989 | European Pat. Off. | C12N 5/00 |
| 0380068A1 | 1/1990 | European Pat. Off. | C12N 15/85 |
| 0362526A2 | 4/1990 | European Pat. Off. | C12N 15/12 |
| 0362531A1 | 4/1990 | European Pat. Off. | C07K 13/00 |
| 0364690A2 | 4/1990 | European Pat. Off. | C07K 15/00 |
| 0365837A2 | 5/1990 | European Pat. Off. | A61K 37/02 |
| 0379904A1 | 8/1990 | European Pat. Off. | C07K 13/00 |
| 0387668A1 | 9/1990 | European Pat. Off. | C12N 15/12 |
| 0387701B1 | 9/1990 | European Pat. Off. | A61K 37/02 |
| 0391088A2 | 10/1990 | European Pat. Off. | A61K 37/02 |
| 0459577A2 | 12/1991 | European Pat. Off. | C07K 15/28 |
| 3712678A1 | 10/1988 | Germany | C12N 5/00 |
| 90/0469 | 10/1990 | Saudi Arabia | |
| 2022826 | 12/1979 | United Kingdom | G01N 33/16 |
| WO 88/06592 | 9/1988 | WIPO | C07H 21/04 |
| WO 89/10938 | 11/1989 | WIPO | C07K 9/00 |
| WO 90/03400 | 4/1990 | WIPO | C07K 15/14 |
| WO 90/10646 | 9/1990 | WIPO | C07K 13/00 |
| WO 90/10652 | 9/1990 | WIPO | C07K 15/14 |
| WO 90/13316 | 11/1990 | WIPO | A61K 39/395 |
| WO 91/16927 | 11/1991 | WIPO | A61K 39/395 |
| WO 91/16928 | 11/1991 | WIPO | A61K 39/395 |
| WO 91/18010 | 11/1991 | WIPO | C07K 5/06 |
| WO 91/18011 | 11/1991 | WIPO | C07K 5/08 |

OTHER PUBLICATIONS

Abraham, G. and Colonno, R. J., "Many Rhinovirus Serotypes Share the Same Cellular Receptor", J. Virol. 51:340–345 (1984).

Anasetti et al., "Activation of Natural Killer Cells by LFA–3 Binding to CD2", Publication, Fred Hutchinson Cancer Research Center, Seattle WA, and Molecular Diagnostics, West Haven, CT (U.S.A.).

Argenbright et al., "Monoclonal Antibodies to the Leukocyte Membrane CD18 Glycoprotein Complex and to Intercellular Adhesion Molecule–1 Inhibit Leukocyte–Endothelial Adhesion in Rabbits", J. Leukoc. Biol. 49:253–257 (1991).

Argenbright, L. W. and Barton, R. W., "Interactions of Leukocyte Integrins with Intercellular Adhesion Molecule–1 in the Production of Inflammatory Vascular Injury In Vivo: the Shwartzman Reaction Revisited", J. Clin. Invest. 89(1):259–272 (1992).

Badger et. al., "Structure Analysis of a Series of Antiviral Agents Complexed with Human Rhinovirus 14", PNAS 85:3304–3308 (1988).

Bangham, C. R. M. and McMichael, A. J., "Nosing ahead in the cold war" Nature 334:16 (1990).

Bebbington, C. R., and Hentschel, C. C. G. "The use of vectors based on gene amplification for the expression of cloned genes in mammalian cells" DNA Cloning 3:163–186 (1987).

Blann, A. D., "Cell Hybrids: an important new source of antibody production" Med. Lab. Sci. 36:329–338 (1979).

Bock et al., "Characterization of soluble forms of NCAM", FEBS Lett 225(1,2):33–36 (1987).

(List continued on next page.)

Primary Examiner—Thomas M. Cunningham

[57] ABSTRACT

The present invention relates to novel forms and configurations of intercellular adhesion molecule (ICAM) including multimeric configurations that effectively bind to human rhinovirus and can effectively reduce HRV infectivity. When in a multimeric configuration, preferably as dimers, these proteins display enhanced binding of HRV and are able to reduce HRV infectivity as well as the infectivity of other viruses known to bind to the "major" group human rhinovirus receptor (HRR). The multimerized proteins may also be used to block tICAM interaction with lymphocyte function-associated antigen-1 (LFA-1).

6 Claims, 13 Drawing Sheets

OTHER PUBLICATIONS

Bowie et al., "Deciphering the Message in Protein Sequences: Tolerance to Amino Acid Substitutions", Science 247:1306–1310 (1990).

Campbell, B. A. and Cords, C. E., "Monoclonal Antibodies That Inhibit Attachment of Group B Coxsackieviruses", J. Virol. 48(2):561–564 (1983).

Capon et al., "Designing CD4 immunoadhesins for AIDS therapy", Nature 337:525–531 (1989).

Cate et al., "Isolation of the Bovine and Human Genes for Müllerian Inhibiting Substance and Expression of the Human Gene in Animal Cells", Cell 45:685–698 (1986).

Cole et al., "Topographic Localization of the Heparin–binding Domain of the Neural Cell Adhesion Molecule N–CAM", J. Cell Biol. 103:1739–1744 (1986).

Colonno et. al., "Isolation of a Monoclonal Antibody that Blocks Attachment of the Major Group of Human Rhinoviruses", J. Virology 57:7–12 (1986).

Colonno, R. J. and Tomassini, J. E., "Viral Receptors: A Novel Approach For The Prevention Of Human Rhinovirus Infection", in Medical Virology VI, de la Maza, L. M. and E. M. Peterson, eds. (Elsevier, New York, 1987) 331–351.

Cooper, G.M., "Cellular Transforming Genes", Science 217:801–806 (1982).

Couch, R.B., "Rhinoviruses", Virology, Second Edition, edited by B. N. Fields, D. M. Knipe et al. Raven Press, Ltd., New York, 607–629 (1990).

Couch et al., "Effect of Route Inoculation on Experimental Respiratory Viral Disease in Volunteers and Evidence for Airborne Transmission", Bacteriol. Rev. 30:517–529 (1966).

Creighton, T.E., Proteins by W. H. Freeman and Company, New York, 33–34 (1984).

Crump et al., "In Vitro Inhibitory Activity of Soluble ICAM–1 for the Numbered Serotypes of Human Rhinovirus", Antiviral Chemistry and Chemother. 4(6):323–327 (1993).

Cunningham et al., "Neural Cell Adhesion Molecule: Structure, Immunoglobulin–Like Domains, Cell Surface Modulation, and Alternative RNA Splicing", Science 236:799–806 (1987).

Cybulsky, M. I. and Gimbrone, Jr., M. A., "Endothelial Expression of a Mononuclear Leukocyte Adhesion Molecule During Atherogenesis", Science 251:788–791 (1991).

D'Alessio et al., "Short–Duration Exposure and the Transmission of Rhinoviral Colds", J. Inf. Dis. 150(2):189–193 (1984).

Deen et al., "A Soluble Form of CD4 (T4) Protein Inhibits AIDS Virus Infection", Nature 331:82–86 (1988).

Dick, E.C., "Experimental Infection of Chimpanzees with Human Rhinovirus Types 14 and 43", Proceedings Of The Society For Experimental Biology And Medicine 127:1079–1081 (1968).

Dochez et al., "Studies in the Common Cold. IV. Experimental Transmission of the Common Cold to Anthropoid Apes and Human Beings by Means of a Filtrable Agent", J. Exp. Med. 52:701–716 (1930).

Douglas et al., "Prophylactic Efficacy of Intranasal Alpha 2–Interferon Against Rhinovirus Infections in the Family Setting", The New England J. of Med. 314:65–70 (1986).

Douglas, R. G., "Pathogenesis of Rhinovirus Common Colds in Human Volunteers", Annals of Otology, Rhinology and Laryngology 79:563–571 (1970).

Dustin et al., "Induction by IL 1 and Interferon–γ: Tissue Distribution, Biochemistry, and Function of a Natural Adherence Molecule (ICAM-1)", J. Immunol. 137(1):245–254 (1986).

Dustin et al., "Supergene Families Meet in the Immune System" Immunology Today, 9(7 and 8):213–215 (1988).

Dustin et al., "Correlation of CD2 Binding and Functional Properties of Multimeric and Monomeric Lymphocyte Function–Associated Antigen 3", J. Exp. Med. 169:503–517 (1989).

Ey, P.L., et. al., "Isolation of Pure IgG1, IgG2a, and IgG2b Immunoglobulins from Mouse Serum Using Protein A–Sepharose", Immunochemistry 15:429–436 (1978).

Fisher et al., "HIV Infection is Blocked in vitro by Recombinant Soluble CD4", Nature 331:76–78 (1988).

Fox et al., "Prevention of a Rhinovirus and Poliovirus Uncoating by WIN 51711, a New Antiviral Drug", Antimicrob. Ag. and Chemotherapy 30:110–116 (1986).

Galfrey et. al., "Antibodies to Major Histocompatibility Antigens Produced by Hybrid Cell Lines", Nature 266:550–552 (1977).

Gething, M.J. and Sambrook, J., "Construction of Influenza Haemagglutinin Genes that Code for Intracellular and Secreted Forms of the Protein" Nature 300:598–603 (1982).

Ginsberg et al., "Inhibition of Fibronectin Binding to Platelets by Proteolytic Fragments and Synthetic Peptides Which Support Fibroblast Adhesion", J. Biol. Chem. 260(7):3931–3936 (1985).

Giranda et al., "Modeling of the Human Intercellular Adhesion Molecule–1, the Human Rhinovirus Major Group Receptor" Proteins: Structure, Function, and Genetics, 7:227–233 (1990).

Gough, N., "Putting A Stop To An Immunoglobulin Message", Trends Genet. 3(9):238–240 (1987).

Gower et al., "Alternative Splicing Generates a Secreted Form of N–CAM in Muscle and Brain", Cell 55:955–964 (1988).

Graham, F.L., and Van der Eb, A. J., "A New Technique for the Assay of Infectivity of Human Adenovirus 5 DNA", Virology 52:456–467 (1973).

Green et al., "Immunogenic Structure of the Influenza Virus Hemagglutinin", Cell 28:477–487 (1982).

Greve et al., "The Major Human Rhinovirus Receptor Is ICAM–1", Cell 56:839–847 (1989).

Greve et al., "Mechanisms of Receptor–Mediated Rhinovirus Neutralization Defined by Two Soluble Forms of ICAM–1", J. Virology 65:6015–6023 (1991).

Gross–Bellard et al., "Isolation of High–Molecular–Weight DNA from Mammalian Cells", Eur. J. Biochem. 36:32–38 (1973).

Güssow, D. and Ploegh, H., "Soluble class I antigens: a conundrum with no solution?", Immunology Today 8(7, 8):220–222 (1987).

Gwaltney et al., Diagnostic Procedures for Viral, Rickettsial and Chlamydial Infections, N. J. Schmidt and R. W. Evans, Eds, 6th edition. p. 603, Am Pub. Health. Assoc., Washington D.C. (1989).

Halperin et al., "Exacerbations of Asthma in Adults During Experimental Rhinovirus Infection", Am. Rev. Respir. Dis. 132:976–980 (1985).

Hamparian et al., "A Collaborative Report: Rhinoviruses– Extension of the Numbering System from 89 to 100", Virology 159:191–192 (1987).

Hardy et al., "Intranasal Drug Delivery by Spray and Drops", J. Pharm. Pharmacol. 37:294–297 (1985).

Harning et al., "Serum Levels of Circulating Intercellular Adhesion Molecule 1 in Human Malignant Melanoma", Cancer Res. 51(8):5003–5005 (1991).

Hayden et al., "Safety and Efficacy of Intranasal Pirodavir (R77975) in Experimental Rhinovirus Infection", Antimicrob. Agents Chemother. 36(4):727–732 (1992).

Hayden et al., "Prevention of Natural Colds by Contact Prophylaxis with Intranasal Alpha2–Interferon", The New England Journal of Medicine, 314(2):71–75 (1986).

Hayden et al., "Modification of Experimental Rhinovirus Colds by Receptor Blockade" Antiviral Research 9:233–247 (1988).

Helenius, A. and Von Bonsdorff, C. H., "Semliki Forest Virus Membrane Proteins, Preparation and Characterization of Spike Complexes Soluble in Detergent–Free Medium" Biochimica et Biophysica Acta 436:895–899 (1976).

Hendley et al., "Relation Between Naturally acquired Immunity and Infectivity of Two Rhinoviruses in Volunteers", J. Inf Dis. 125:243–248 (1972).

Holland, J. J. and McLaren, L. C., "The mammalian cell–virus relationship. II. Absorption, Reception and Eclipse of Poliovirus by HeLa Cells" J. Exp. Med. 109:487–504 (1959).

Holland, J. J., "Receptor affinities as Major Determinants of Enterovirus Tissue Tropisms in Humans", Virology 15:312–326.

Horton et al., "Gene Splicing by Overlap Extension: Tailor–Made Genes Using the Polyerase Chain Reaction", Bio-Techniques 8(5):528–535 (1990).

Hussey et. al., "A Soluble CD4 Protein Selectively Inhibits HIV Replication and Syncytium Formation" Nature, 331:78–81 (1988).

Illum, L., "The Nasal Delivery of Peptides and Proteins", Trends in Biotech. 9:284–289 (1991).

Johnston et al., "Viruses as Precipitants of Asthma Symptoms. III. Rhinoviruses: Molecular Biology and Prospects for Future Intervention", Clin. Exp. Allergy, 23:237 (1993).

Johnston et al., "Viral Infections in Exacerbations in School Children with Cough or Wheeze: A Longitudinal Study", Am. Rev. Resp. Dis., 145:A546 (1992).

Kamarck, M. E., and Ruddle, F. H., "Somatic Cell Genetics and the Human Gene Map", Chapter 105 in *Handbook of Experimental Immunology in Four Volumes, vol. 3: Genetics and Molecular Immunology*, D. M. Weir, ed. (Blackwell Scientific Publications, Boston, MA, 1986).

Katz et al., "Chromosome Mapping of Cell Membrane Antigens Expressed on Activated B Cells", Eur. J. Immunol., 15:103–106 (1985).

Kavenoff, R., and Zimm, B. H., "Chromosome–Sized DNA Molecules from Drosophila", Chromosoma (Berl.) 41:1–27 (1973).

Kühn et al., "Gene Transfer, Expression, and Molecular Cloning of the Human Transferrin Receptor Gene", Cell 37:95–103 (1984).

Lebman et al., "A Monoclonal Antibody that Detects Expression of Transferrin Receptor in Human Erythroid Precursor Cells", Blood 59(3):671–678 (1982).

Lemanske et al., "Rhinovirus Upper Respiratory Infection Increases Airway Hyperreactivity and Late Asthmatic Reactions", J. Clin. Invest. 83:1–10 (1989).

Littlefield, J.W., "Selection of Hybrids from Matings of Fibroblasts in vitro and Their Presumed Recombinants", Science 145:709–710 (1964).

Lonberg–Holm et al., "Unrelated Animal Viruses Share Receptors", Nature 259:679–681 (1976).

Margulies, D. H., et. al., "Engineering Soluble Major Histocompatibility Molecules: Why and How", Immunol. Res. 6: 101–116 (1987).

Marlin, S.D. and Springer, T. A., "Purified Intercellular Adhesion Molecule–1 (ICAM–1) Is a Ligand for Lymphocyte Function–Associated Antigen 1 (LFA–1)", Cell 51:813–819 (1987).

Marlin et al., "A Soluble Form of Intercellular Adhesion Molecule–1 Inhibits Rhinovirus Infection", Nature 344:70–72 (1990).

Marsh et al., "Antibody–toxin Conjugation", *Immunotoxins* by Kluwer Academic Publishers, Boston, Dordrecht, Lancaster 213–237 (1988).

Marsh et al., "Interactions of Semliki Forest Virus Spike Glycoprotein Rosettes and Vesicle with Cultures Cells", J. Cell Biology 96:455–461 (1983).

McClelland et al., "Identification of Monoclonal Antibody Epitopes and Critical Residues for Rhinovirus in Domain 1 of ICAM–1", PNAS 88(18):7993–7997 (1991).

McClelland et al., "Transfectant cell lines which express the major human rhinovirus receptor, their preparation, and their uses", Chemical Abstracts 112:117175h (1990).

McCray, J. and Werner, G., "Different Rhinovirus Serotypes Neutralized by Antipeptide Antibodies", Nature 329:736–738 (1987).

Medical Microbiology: "An Introduction to Infectious Diseases", 2nd ed., J.C. Sherris, ed. (Elsevier Science Publishing Co., Inc., N.Y. 1990) pp. 514–515.

Medrano, L. and Green, H., "Picornavirus Receptors and Picornavirus Multiplication in Human–Mouse Hybrid Cell Lines", Virology 54:515–524 (1973).

Melchers et al., *Lymphocyte hybridomas*, vol. 81 of Current Topics in Microbiology and Immunology, W. Arber, W. Henle, P.H. Hofschneider, J.H. Humphrey, J. Klein, P. Koldovsky, H. Koprowski, O. Maaloe, F. Melchers, R. Rott, H.G. Schweiger, L. Syrucek, P.K. Vogt, eds (Springer Verlang, New York, 1978).

Mendelsohn et al., "Transformation of a Human Poliovirus Receptor Gene into Mouse Cells", PNAS 83:7845–7849 (1986).

Minor, P.D., "Growth, Assay and Purification of Picornaviruses", in *Virology: A Practical Approach*, B.W.J. Mahy, ed. (IRL Press Limited, Oxford, England), 25–41 (1985).

Minor et al., "Monoclonal antibodies which block cellular receptors of poliovirus", Virus Research 1:203–212 (1984).

Morein, B., "Potentiation of the Immune Response by Immunization with Antigens in Defined Multimeric Physical Forms", Veterinary Immunology and Immunopathology 17:153–159 (1987).

Niman et al., "Anti–peptide antibodies detect oncogene–related proteins in urine", PNAS 82:7924–7928 (1985).

Nobis et al., "Production of a Monoclonal Antibody against an Epitope on HeLa Cells that Is the Functional Poliovirus Binding Site", J. Gen. Virol. 66:2563–2569 (1985).

Ohlin et al., "Spectrum of Activity of Soluble Intercellular Adhesion Molecule–1 Against Rhinovirus Reference Strains and Field Isolates", Antimicrob. Agents and Chemother. 38:1413–1415 (1994).

Parham, P., "Monoclonal Antibodies Against HLA Products and Their use in Immunaffinity Purification," Methods in Enzymology 92:110–138 (1983).

Pepinsky et al., "The Increased Potency of Crossed–linked Lymphocyte Function–associated Antigen-3 (LFA–3) Multimers Is a Direct Consequence of Changes in Valency", J. Biol. Chem. 266 (27):18244–18249 (1991).

Peterson, A. and Seed, B., "Genetic Analysis of Monoclonal Antibody and HIV Binding Sites on the Human Lymophocyte Antigen CD4", Cell 54:65–72 (1988).

Rossman et al., "Structure of a Human Common Cold Virus and Functional Relationship to other Picornaviruses", Nature 317:145–153 (1985).

Rothlein et al., "A Form of Circulating ICAM–1 In Human Serum", J. Immuno. 147(11):3788–3793 (1991).

Rothlein et al., "A Human Intercellular Adhesion Molecule (ICAM–1) Distinct From LFA–1", J. Immuno. 137(4):1270–1274 (1986).

Ruddle et al., "DNA–Mediated Gene Transfer in Mammalian Gene Cloning", Genetic Engineering 6:319–338 (1984).

Ruoslahti et al., "Synthetic Peptides in the Analysis of Cell Adhesion," in *Synthetic Peptides in Biology and Medicine* Elsvier Science Publishers, pp. 191–197 (1985).

Saiki et al., "Enzymatic Amplification of β–Globin Genomic Sequences and Restriction Site Analysis for Diagnosis of Sickle Cell Anemia," Science 230:1350–1354 (1985).

Sambrook et al., *Molecular Cloning: A Laboratory Manual*, 2d ed. (Cold Spring Harbor Laboratory Press, Cold Spring Harbor, NY, 1989) pp. 1.21–1.52.

Schipper et al., "The Nasal Mucocilliary Clearance: Relevance to Nasal Drug Delivery", Pharm. Res. 8:807–814 (1991).

Scopes, R.K., "Separation By Precipitation," in *Protein Purification: Principles & Practice* (1982) Springer Verlag, NY, pp. 39–46.

Seed, B. and Aruffo, A., "Molecular Cloning of the CD2 antigen, the T–Cell Erythrocyte Receptor, by a Rapid Immunoselection Procedure," PNAS 84:3365–3369 (1987).

Seed, B., "An LFA–3 cDNA Encodes a Phospholipid–Linked Membrane Protein Homologous to its Receptor CD2," Nature 329:840–842 (1987).

Seth et al., "Circulating ICAM–1 isoforms: Diagnostic Prospects for Inflammatory and Immune Disorders," Lancet 338:83–84 (1991).

Sherman–Gold, R., "Companies Pursue Therapies Based on Complex Cell Adhesion Molecules", Genetic Engineering News pp. 6–7,14 (Jul. 1993).

Sherry, B. and Rueckert, R., "Evidence for at Least Two Dominant Neutralization Antigens on Human Rhinovirus 14," J. Virol. 53(1):137–143 (1985).

Shih, C. and Weinberg, R. A., "Isolation of a Transforming Sequence from a Human Bladder Carcinoma Cell Line," Cell 29:161–169 (1982).

Shipkowitz et al., "Antiviral Activity of a bis–Benzimidazole Against Experimental Rhinovirus Infections in Chimpanzees", App. Microbiol. 23(1):117–122 (1972).

Siddique et al., "The Poliovirus Sensitivity (PVS) Gene Is on Chromosome 19q12->q13.2", Genomics 3:156–160 (1988).

Simmons et al , "ICAM, an Adhesion Ligand of LFA–1, is Homologous to the Neural Cell Adhesion Molecule NCAM," Nature 331:624–627 (1988).

Simons et al., "Formation of Protein Micelles from Amphiphilic Membrane Proteins", PNAS 75(11):5306–5310 (1978).

Skerra, A. and Pluckthun, A., "Assembly of a Functional Immunoglobulin FV Fragment in *Escherichia coli*" Science, 240:1038–1041 (1988).

Smith, T.J., et. al., "The Site of Attachment in Human Rhinovirus 14 for 4 Antiviral Agents that Inhibit Uncoating", Science 233:1286–1293 (1986).

Smith et al., "Blocking of HIV–1 Infectivity by a Soluble, Secreted Form of the CD4 Antigen," Science 238:1704–1707 (1987).

Smith et al., "Modification and Secretion of Human Interleukin 2 Produced in Insect Cells by a Baculovirus Expression Vector", PNAS 82:8404–8408 (1985).

Springer, T.A., "Adhesion Receptors of the Immune System", Nature 346:425–434 (1990).

Staunton et al., "Primary Structure of ICAM–1 Demonstrates Interaction between Members of the Immunoglobulin and Integrin Supergene Families," Cell 52:925–933 (1988).

Staunton et al., "The Arrangement of the Immunoglobulin–Like Domains of ICAM–1 and the Binding Sites for LFA–1 and Rhinovirus," Cell 61:243–254 (1990).

Staunton et al., "A Cell Adhesion Molecule, ICAM–1, is the Major Surface Receptor for Rhinoviruses," Cell 56:849–853 (1989).

Steis et al., "Serum Soluble IL–2 Receptor as a Tumor Marker in Patients with Hairy Cell Leukemia", Blood 71(5):1304–1309 (May 1988).

Sundquist et al., "Influenza Virus ISCOMs: Antibody Response in Animals", Vaccine 6:49–53 (1988).

Sundquist et al., "Influenza Virus ISCOMs: Biochemical Characterization", Vaccine 6:44–48 (1988).

Tomassini, J.E., "Isolation, Characterization and Cloning of the Cellular Receptor for the Major Group of Human Rhinoviruses," Ph.D. Thesis, University of Pennsylvania (1986).

Tomassini, J.E. and Colonno, R. J., "Isolation of a Receptor Protein Involved in Attachment of Human Rhinoviruses," J. Virol. 58(2):290–295 (1986).

Tomassini et al., "CDNA Cloning Reveals that the Major Group Rhinovirus Receptor on HeLa Cells is Intercellular Adhesion Molecule 1," PNAS 86:4907–4911 (1989).

Towbin et. al., "Electrophoretic Transfer of Proteins from Polyacrylamide Gels to Nitrocellulose Sheets: Procedure and Some Applications", PNAS 76(9):4350–4354 (1979).

Traunecker et al., "Highly Efficient Neutralization of HIV with Recombinant CD4–Immunoglobulin Molecules," Nature 339: 68–70 (1989).

Traunecker et al., "Soluble CD4 Molecules Neutralize Human Immunodeficiency Virus Type 1" Nature 331:84–86 (1988).

Turner et al., "Efficacy of Oral WIN 54954 for Prophylaxis of Experimental Rhinovirus Infection", 37:297–300 (1993).

Urlaub, G. and Chasin, L. A., "Isolation of Chinese Hamster Cell Mutants Deficient in Dihydrofolate Reductase Activity," PNAS USA 77(7):4216–4220 (1980).

Wade, N., "Hybridomas: A Potent New Biotechnology," Science 208:692–693 (1980).

Welsh, K.I., "Antibody Production Made Easier," Nature 266:495 (1977).

Wigler et al., "Transformation of Mammalian Cells with Genes from Procaryotes and Eucaryotes," Cell 16:777–785 (1979).

Williams, A. F., "A Year in the Life of the Immunoglobulin Superfamily", Immunology Today 8(10):298–303 (1987).

Williams, A. F. and Barclay, A. N., "The Immunoglobulin Superfamily–Domains for Cell Surface Recognition[1,2]", Ann. Rev. Immunol. 6:381–405 (1988).

Winther et al., "Sites of Rhinovirus Recovery After Point Inoculation of the Upper Airway", JAMA 256(13):1763–1767 (1986).

Woods et al., "In Vitro and In Vivo Activities of WIN 54954, a New Broad Spectrum Antipicornavirus Drug", Antimicrob. Agents Chemother 33:2069–2074 (1989).

Zettlmeissl et al., "Expression and Characterization of Human CD4: Immunoglobulin Fusion Proteins," DNA and Cell Biology 9:347–353 (1990).

Braude, A. (ed.s), "Infectious Diseases and Medical Microbiology, 2nd edition, W.B. Saunders Co., Philadelphia, PA, (1986) chapter 65 Picornaviruses", pp. 521–529.

Gennaro, A.R. (ed.), Remington's Pharmaceutical Sciences, 18th edition, Mack Publishing Co., Easton, PA (1990), "Drug Absorption, Action and Disposition", pp. 707–721.

Martin et al., "Efficient Neutralization and Disruption of Rhinovirus by Chimeric ICAM–1 Immunoglobulin Molecules", J. Virology, 67(6):3561–3568 (Jun. 1993).

Hendley et al., "Transmission of Rhinovirus Colds By Self–Inoculation", The New England Journal of Medicine, 288(26):1361–1364 (Jun. 28, 1973).

Hendley, J. O., and Gwaltney, J. M., Jr., "Mechanisms of Transmission of Rhinovirus Infections", Epidemiologic Reviews, 10:242–257 (1988).

Suter, David, Associated Press, "Tests for a Nasal Spray to Deflect Cold Viruses", New York Times, Sep. 20, 1995.

Manning, Anita, "War on Bacteria Mix of Victories Amid Warnings", USA Today, Sep. 20, 1995.

Haney, Daniel Q., "Beyond Chicken Soup. Nasal Spray Keeps Chimps From Catching Cold Virus", St. Louis Post Dispatch, Sep. 20, 1995.

Associated Press, "Common Colds: Nasal Spray May Help Keep The Sniffles Away", Atlanta Constitution, Sep. 20, 1995.

Associated Press, "Drug Sprays Away Colds", New York Post, Sep. 20, 1995.

Haney, Daniel Q., Associated Press, "The Cold War: Scientists Develop Spray That May End Sniffles", Arizona Republic, Sep. 20, 1995.

Haney, Daniel Q., Associated Press, "For Colds, Nasal Spray Holds Hope. A Protein Swamps The Virus With Potential Targets In The Nose. Its a Decoy Trick", Philadelphia Inquirer, Sep. 20, 1995.

Associated Press, "Simple Nasal Spray May Be Able To Keep Common Cold Away. Medicine Successful On Chimps So Far", Washington Times, Sep. 20, 1995.

Associated Press, "Doctors Sniffing Out Spray to Fight Colds", Denver Post, Sep. 20, 1995.

Associated Press, "Someday Soon, A Simple Sniff Should Snuff The Sniffles", Houston Chronicle, Sep. 20, 1995.

Haney, Daniel Q., Associated Press, "Spray May Ward Off Sniffles. Nasal Treatment Studied To Keep Cold Viruses From Invading Victim", Denver–Rocky Mountain News, Sep. 20, 1995.

Haney, Daniel Q., Associated Press, "Scientists Make Headway In Cold War With Nose On Spray", Chicago Sun-Times, Sep. 20, 1995.

Haney, Daniel Q., Associated Press, "Labs Busy Working Nose Spray To Keep Colds Away", Charlotte Observer, Sep. 20, 1995.

Associated Press, "Nasal Spray May Prevent Sniffles", Miami Herald, Sep. 20, 1995.

Associated Press, "Cure For The Cold? No, But Prevention May Be Spray Away", San Diego Union–Tribune, Sep. 20, 1995.

Haney, Daniel Q., "Nasal Spray Touted As Next–Best Thing To Cure For Colds", The Montreal Gazette, Sep. 20, 1995.

Associated Press, "Scientists Feel They Can Develop Spray To Keep The Sniffles Away", The Spectator, Sep. 20, 1995.

Haney, Daniel Q., Associated Press, "New Nasal Spray May Take Sniffles Out Of Common Cold", Cleveland Plain Dealer, Sep. 20, 1995.

Associated Press, "No Cure, But Nothing To Sniff(le) At. Nasal Spray To Block Common Cold Is In The Works", Minneapolis Star Tribune, Sep. 20, 1995.

Haney, Daniel Q., Associated Press, "Out Front: Progress On Cold Front. Spray May Ward Off Sniffles. Medicine Is First To Block Infection", Sep. 19 1995.

Monitoring Report, "Cure For Colds 9/18 to 9/20", Video Monitoring Services of America, a Burrelle's Affiliate, New York, New York, pp. 1–3, Sep. 20, 1995.

Intercellular adhesion molecule-1 (ICAM-1)

```
                        5                          10
    Asn Ala Gln Thr Ser Val Ser Pro Ser Lys
                                           ---

15                          20
    Val Ile Leu Pro Arg Gly Gly Ser Val Leu
    |--------- 94 --->

25                          30
    Val Thr Cys Ser Thr Ser Cys Asp Gln Pro 35                          40
    Lys Leu Leu Gly Ile Glu Thr Pro Leu Pro 45                          50
    Lys Lys Glu Leu Leu Leu Pro Gly Asn Asn
    ----|--- ---- 94&96 ------------------

55                          60
    Arg Lys Val Tyr Glu Leu Ser Asn Val Gln
    --->|--- ------ (25k) — 91&115&142&147 ----

65                          70
    Glu Asp Ser Gln Pro Met Cys Tyr Ser Asn
    ──────────────────────────────  ───  ─── ───

75                          80
    Cys Pro Asp Gly Gln Ser Thr Ala Lys Thr
    ───         ---- ---                --->

85                          90
    Phe Leu Thr Val Tyr Trp Thr Pro Glu Arg
```

FIG. IA

```
                            95                              100
     Val Glu Leu Ala Pro Leu Pro Ser Trp Gln 105                             110
     Pro Val Gly Lys Asn Leu Thr Leu Arg Cys 115                             120
     Gln Val Glu Gly Gly Ala Pro Arg Ala Asn 125                             130
     Leu Thr Val Val Leu Leu Arg Gly Glu Lys
                                                     ---

135                             140
     Glu Leu Lys Arg Glu Pro Ala Val Gly Glu
      |  ———————— (34k) — 103&114&121&135 ——

145                             150
     Pro Ala Glu Val Thr Thr Thr Val Leu Val
     ——————————————————————— (xx) ———————————

155                             160
     Arg Arg Asp His His Gly Ala Asn Phe Ser
     --------------    ------------    --->

165                             170
     Cys Arg Thr Glu Leu Asp Leu Arg Pro Gln 175                             180
     Gly Leu Glu Leu Phe Glu Asn Thr Ser Ala
```

FIG. IB

```
                      185                              190
       Pro Tyr Gln Leu Gln Thr Phe Val Leu Pro 195                              200
       Ala Thr Pro Pro Gln Leu Val Ser Pro Arg
                                               ---

205                              210
       Val Leu Glu Val Asp Thr Gln Gly Thr Val
        |(x) ——————— (50k) — 110 ———————————————

215                              220
       Val Cys Ser Leu Asp Gly Leu Phe Pro Val
       ———     ——————————————————————————————————

225                              230
       Ser Glu Ala Gln Val His Leu Ala Leu Gly
       ————  ——————————       ———   ————   ——→

235                              240
       Asp Gln Arg Leu Asn Pro Thr Val Thr Tyr 245                              250
       Gly Asn Asp Ser Phe Ser Ala Lys Ala Ser 255                              260
       Val Ser Val Thr Ala Glu Asp Glu Gly Thr 265                              270
       Gln Arg Leu Thr Cys Ala Val Ile Leu Gly
```

FIG. IC

|     |     |     |     | 275 |     |     |     | 280 |
| --- | --- | --- | --- | --- | --- | --- | --- | --- |
| Asn | Gln | Ser | Gln | Glu | Thr | Leu | Gln | Thr | Val |

|     |     |     |     | 285 |     |     |     | 290 |
| --- | --- | --- | --- | --- | --- | --- | --- | --- |
| Thr | Ile | Tyr | Ser | Phe | Pro | Ala | Pro | Asn | Val |

|     |     |     |     | 295 |     |     |     | 300 |
| --- | --- | --- | --- | --- | --- | --- | --- | --- |
| Ile | Leu | Thr | Lys | Pro | Glu | Val | Ser | Glu | Gly |

|     |     |     |     | 305 |     |     |     | 310 |
| --- | --- | --- | --- | --- | --- | --- | --- | --- |
| Thr | Glu | Val | Thr | Val | Lys | Cys | Glu | Ala | His |

|     |     |     |     | 315 |     |     |     | 320 |
| --- | --- | --- | --- | --- | --- | --- | --- | --- |
| Pro | Arg | Ala | Lys | Val | Thr | Leu | Asn | Gly | Val |

|     |     |     |     | 325 |     |     |     | 330 |
| --- | --- | --- | --- | --- | --- | --- | --- | --- |
| Pro | Ala | Gln | Pro | Leu | Gly | Pro | Arg | Ala | Gln |

|     |     |     |     | 335 |     |     |     | 340 |
| --- | --- | --- | --- | --- | --- | --- | --- | --- |
| Leu | Leu | Leu | Lys | Ala | Thr | Pro | Glu | Asp | Asn |

|     |     |     |     | 345 |     |     |     | 350 |
| --- | --- | --- | --- | --- | --- | --- | --- | --- |
| Gly | Arg | Ser | Phe | Ser | Cys | Ser | Ala | Thr | Leu |

|     |     |     |     | 355 |     |     |     | 360 |
| --- | --- | --- | --- | --- | --- | --- | --- | --- |
| Glu | Val | Ala | Gly | Gln | Leu | Ile | His | Lys | Asn |

FIG.1D

```
                        365                          370
        Gln Thr Arg Glu Leu Arg Val Leu Tyr Gly 375                          380
        Pro Arg Leu Asp Glu Arg Asp Cys Pro Gly 385                          390
        Asn Trp Thr Trp Pro Glu Asn Ser Gln Gln 395                          400
        Thr Pro Met Cys Gln Ala Trp Gly Asn Pro 405                          410
        Leu Pro Glu Leu Lys Cys Leu Lys Asp Gly
                                        ----|-------

415                          420
        Thr Phe Pro Leu Pro Ile Gly Glu Ser Val
        ---- ——————— 97&46 ————————————————————

425                          430
        Thr Val Thr Arg Asp Leu Glu Gly Thr Tyr
        ————————————————————————————————————— —

435                          440
        Leu Cys Arg Ala Arg Ser Thr Gln Gly Glu
        ——— (xx) ——————————— --->

445                          450
        Val Thr Arg Glu Val Thr Val Asn Val Leu
```

FIG. IE

```
                        455                          460
Ser Pro Arg Tyr Glu Ile Val Ile Ile Thr 465                          470
Val Val Ala Ala Ala Val Ile Met Gly Thr 475                          480
Ala Gly Leu Ser Thr Tyr Leu Tyr Asn Arg 485                          490
Gln Arg Lys Ile Lys Lys Tyr Arg Leu Gln
                    ----|--- ——————— 96 ———
                ————|————————— ——— 94 ———

495                          500
Gln Ala Gln Lys Gly Thr Pro Met Lys Pro
——————————————————>|———— ——— 91&142 ———————
——————————————— ———>

505
Asn Thr Gln Ala Thr Pro Pro
——————————————————>
```

FIG. IF

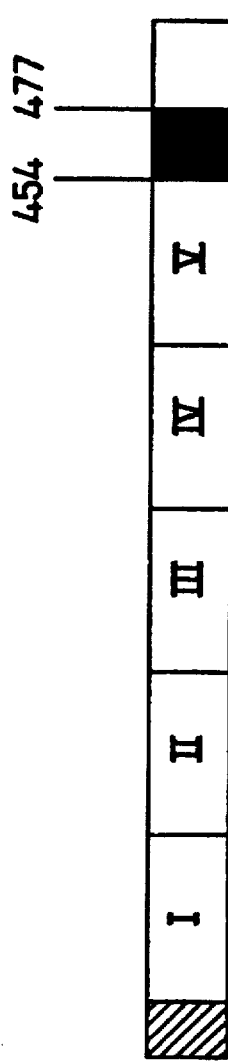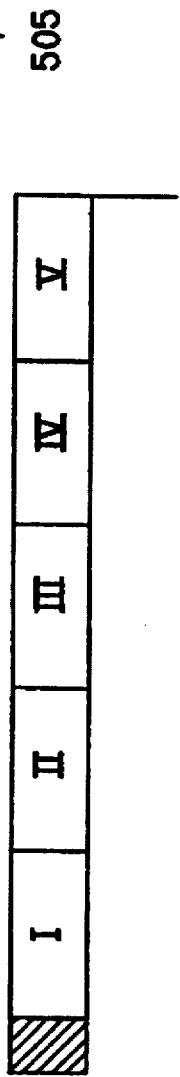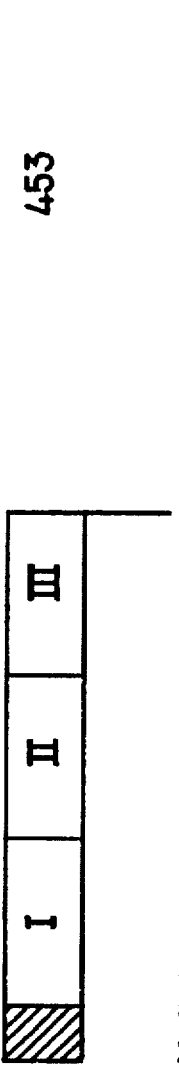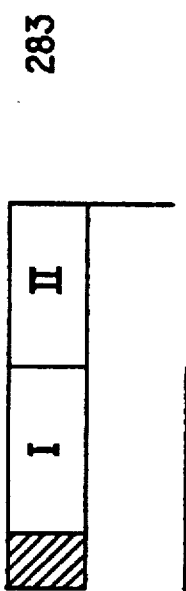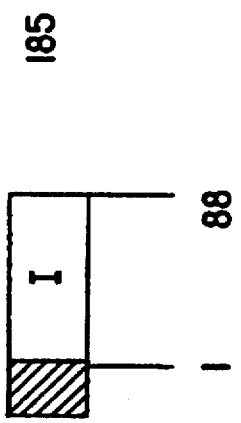
FIG. 2A tmICAM-1   FIG. 2B tICAM(453)   FIG. 2C tICAM(283)   FIG. 2D tICAM(185)   FIG. 2E tICAM(88)

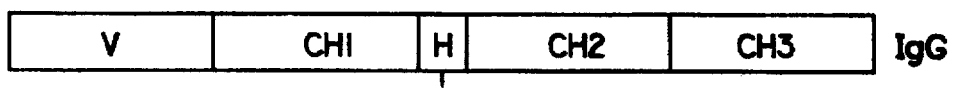
FIG. 3A
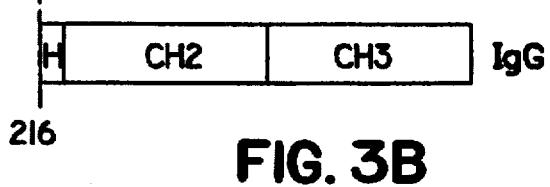
216
FIG. 3B
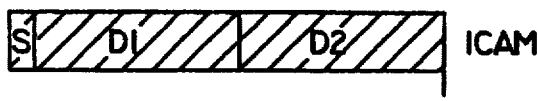
185
FIG. 3C
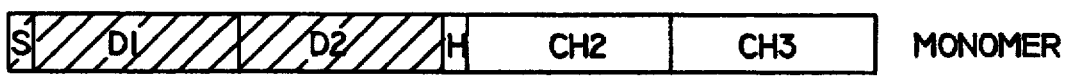
FIG. 3D
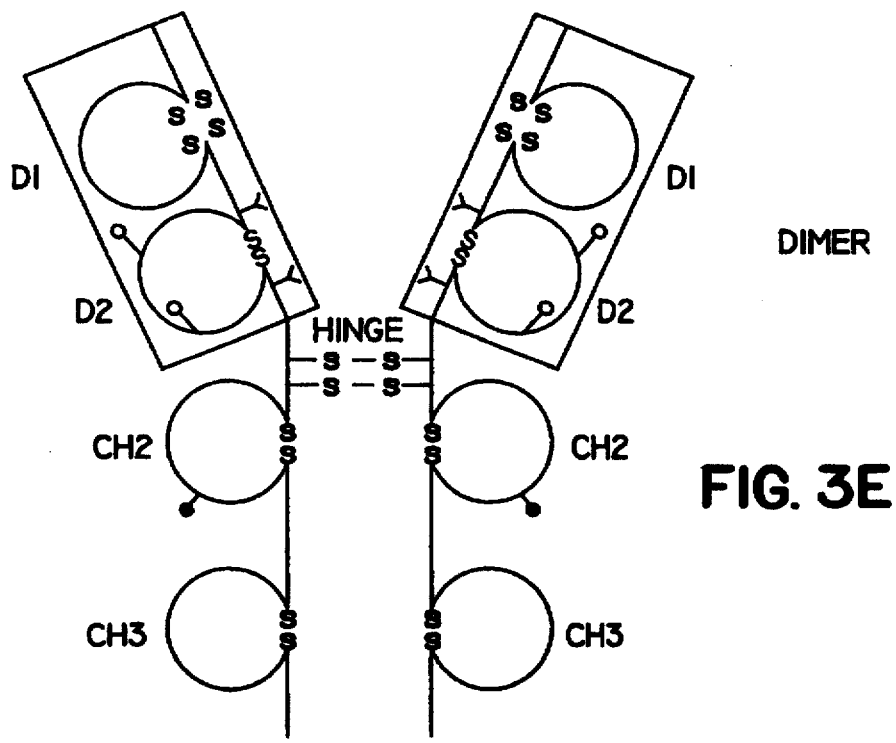
FIG. 3E FIG.4A
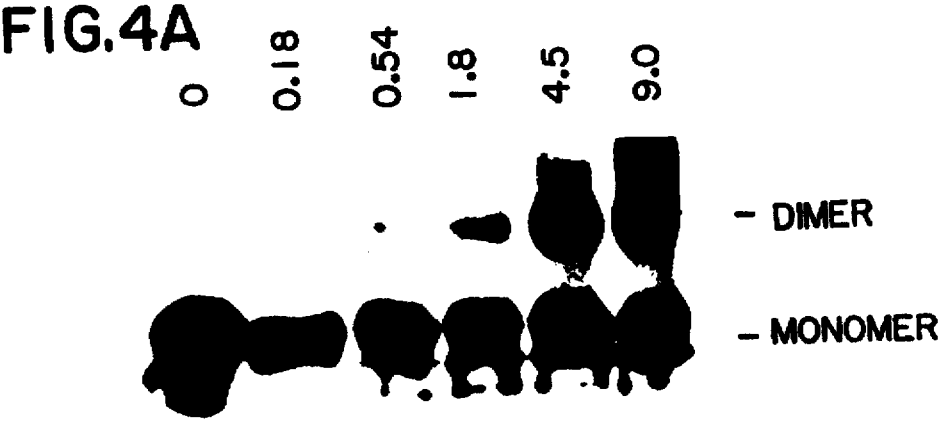
FIG.4B
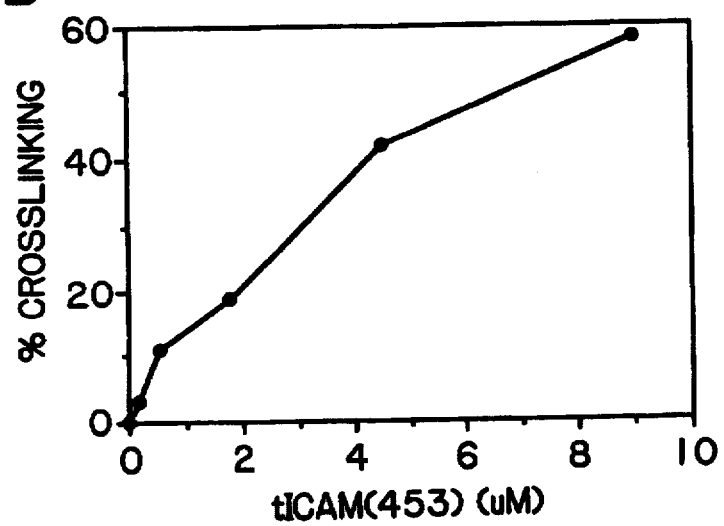
FIG.4C tICAM(1-451)

LFA-3  210  237

LFA-3(210-237)

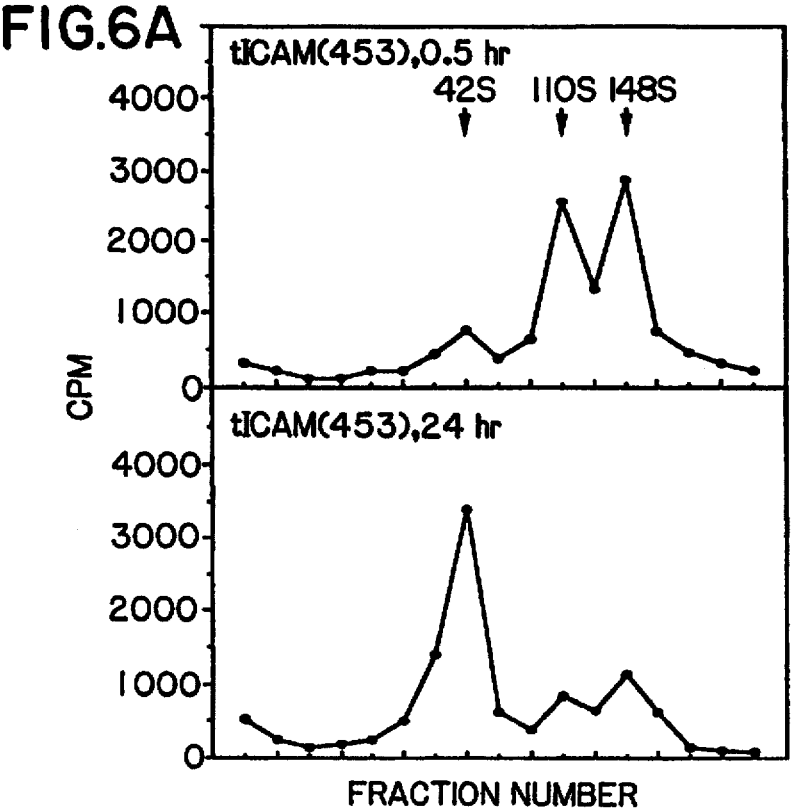
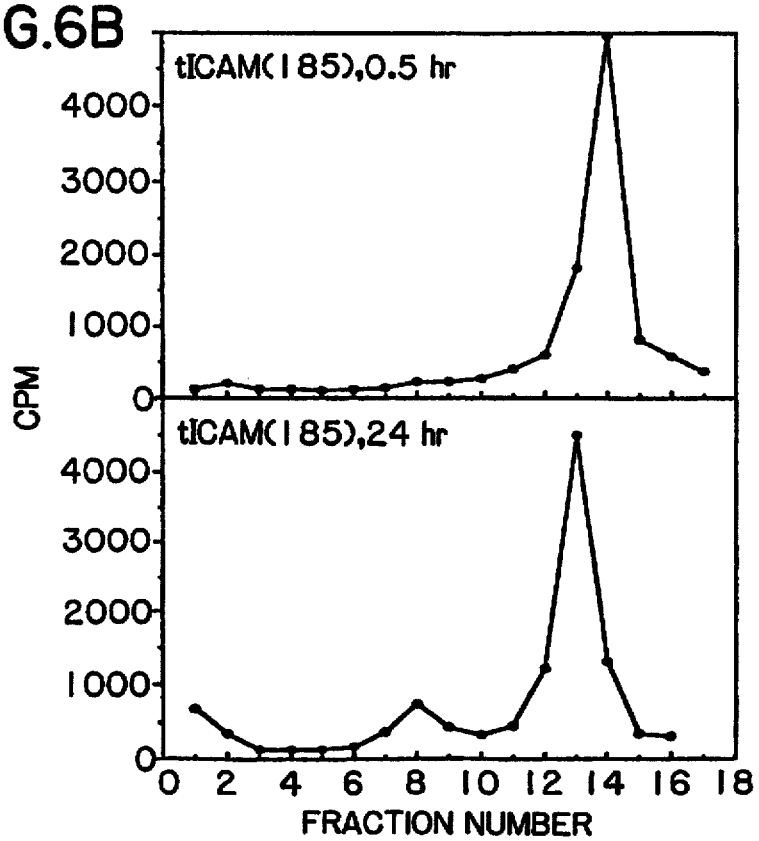

- VP1
- VP2 & VP3
- VP4

● HRV3 RNA
● 148S
● 110S
  42S

ICAM-1 Domain 4
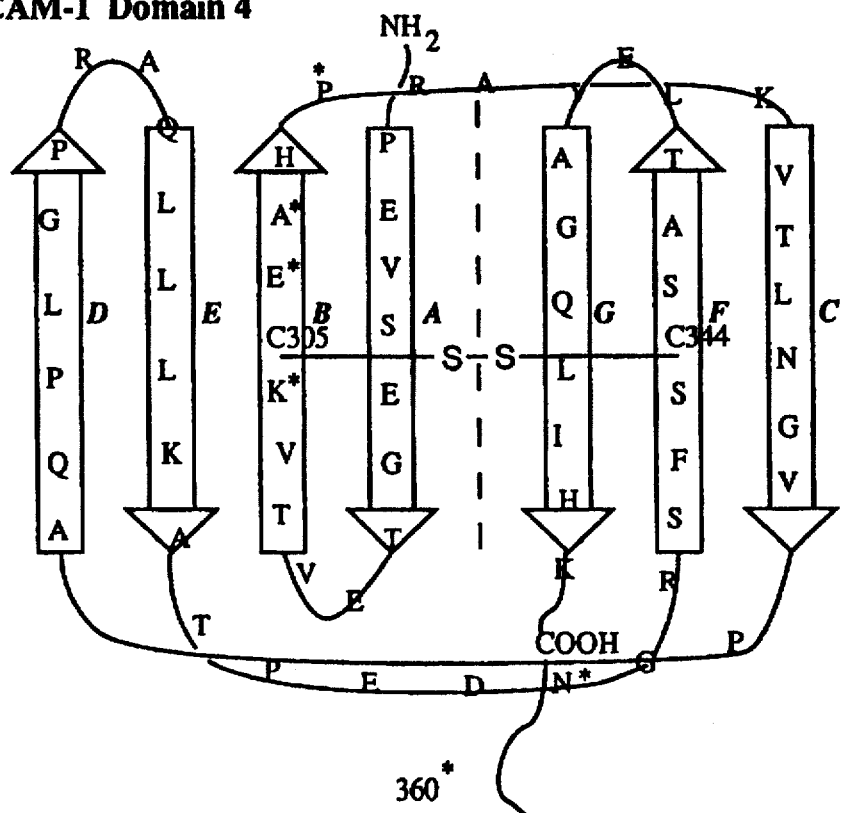
ICAM-1 Domain 5
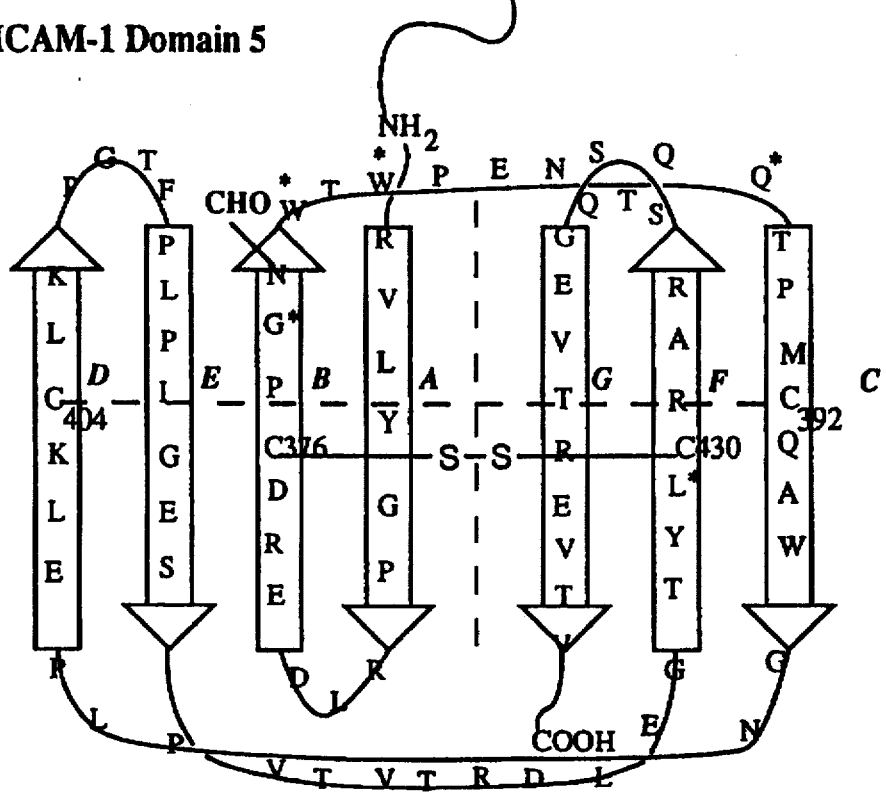
FIG. 7

MULTIMERIC FORMS OF HUMAN RHINOVIRUS RECEPTOR PROTEIN

This is a continuation of copending U.S. application Ser. No. 08/318,038, filed 4 Oct. 1994, which is a continuation of U.S. Ser. No. 08/171,261, filed 21 Dec. 1993, abandoned, which is a continuation of U.S. Ser. No. 07/977,590, filed 17 Nov. 1992, abandoned, which is a continuation of U.S. Ser. No. 07/704,984, filed 24 May 1991, abandoned, which is a continuation-in-part of U.S. Ser. No. 07/556,238, filed 20 Jul. 1990, abandoned.

BACKGROUND OF THE INVENTION

The present invention relates to novel forms and multimeric configurations of intercellular adhesion molecule (ICAM), including both full-length and truncated forms of these proteins, that effectively bind to human rhinovirus and can effectively reduce HRV infectivity, and to methods of making and using same.

Full-length ICAM, also known as human rhinovirus receptor (HRR), is termed transmembrane ICAM (tmICAM-1); non-transmembrane ICAM forms, also known as truncated ICAM (tICAM), are less than full length. When in a multimeric configuration, preferably as dimers, these proteins display enhanced binding of human rhinovirus (HRV) and are able to reduce HRV infectivity. In addition, these multimerized proteins may also be used to reduce infectivity of other viruses that are known to bind to the 'major' group human rhinovirus receptor (HRR), such as Coxsackie A virus, and may also be used to block transmembrane intercellular adhesion molecule (tmICAM) interaction with lymphocyte function-associated antigen-1 (LFA-1), which is critical to many cell adhesion processes involved in the immunological response. Lastly, these multimerized proteins may be used to study the ICAM-1/HRV interaction especially with respect to designing other drugs directed at affecting this interaction.

Human rhinoviruses are the major causative agent of the common cold. They belong to the picornavirus family and can be classified based on the host cell receptor to which they bind. Tomassini, et al., J. Virol., 58: 290 (1986) reported the isolation of a receptor protein involved in the cell attachment of human rhinovirus. Approximately 90% of the more than 115 serotypes of rhinoviruses, as well as several types of Coxsackie A virus, bind to a single common receptor termed the "major" human rhinovirus receptor (HRR); the remaining 10% bind to one or more other cell receptors.

Recently, Greve, J. et al., Cell, 56:839 (1989), co-authored by the co-inventors herein, identified the major HRR as a glycoprotein with an apparent molecular mass of 95,000 daltons and having an amino acid sequence essentially identical to that deduced from the nucleotide sequence of a previously described cell surface protein named intercellular adhesion molecule (ICAM-1). See FIG. 1. Simmons, D. et al., Nature, 331:624 (1988). Staunton, et al., Cell, 52:925–933 (1988). Subsequently, Staunton, D. E., et al., Cell, 56:849 (1989), confirmed that ICAM-1 is the major surface receptor for HRV. See also, Staunton, et al., Cell, 61:243–254 (1990).

ICAM-1 is an integral membrane protein 505 amino acids long and has: i) five immunoglobulin-like extracellular domains at the amino-terminal end (amino acid residues 1–453), ii) a hydrophobic transmembrane domain (454–477), and iii) a short cytoplasmic domain at the carboxy-terminal end (478–505). See FIG. 2. ICAM-1 is a member of the immunoglobulin supergene family and functions as a ligand for the leukocyte molecule, lymphocyte function associated molecule-1 (LFA-1), a member of the integrin family. Heterotypic binding of LFA-1 to ICAM-1 mediates cellular adhesion of diverse cell types and is important in a broad range of immune interactions; induction of ICAM-1 expression by cytokines during the inflammatory response may regulate leukocyte localization to inflammatory sites. The primary structure of ICAM-1 has been found to be homologous to two cellular adhesion molecules, i.e., neural cell adhesion molecule (NCAM) and mylein-associated glycoprotein (MAG).

Several approaches to decreasing infectivity of viruses in general, and of rhinovirus in particular, have been pursued including: i) developing antibody to the cell surface receptor for use in blocking vital binding to the cell, ii) using interferon to promote an anti-viral state in host cells; iii) developing various agents to inhibit viral replication; iv) developing antibodies to viral capsid proteins/peptides; and v) blocking viral infection with isolated cell surface receptor protein that specifically blocks the viral binding domain of the cell surface receptor.

Using this latter approach, Greve, et al., Cell, 56:879 (1989), supra, reported that purified tmICAM-1 could bind to rhinovirus HRV3 in vitro. Unpublished results with HRV2, HRV3, and HRV14 demonstrate a positive correlation between the ability to bind to rhinovirus and the ability to neutralize rhinovirus particularly if the binding studies are carried out under conditions where ICAM-1 is presented in a particular form and configuration as discussed further, infra. Results (unpublished) using HRV14 and HRV2 demonstrate a positive correlation between the receptor class of the virus and the ability to bind to tmICAM-1 in vitro. That is, ICAM-1, being the major receptor, can bind to HRV3, HRV14, and other "major" receptor serotypes and neutralize them, while it does not bind or neutralize HRV2, a "minor" receptor serotype. Further studies (unpublished), using purified tmICAM-1, demonstrate that it effectively inhibits rhinovirus infectivity in a plaque-reduction assay when the rhinovirus is pretreated with tmICAM-1 (50% reduction of titer at 10 nM receptor and one log reduction of titer at 100 nM receptor protein). These data were consistent with the affinity of rhinovirus for ICAM-1 of HeLa cells, which had an apparent dissociation constant of 10 nM, and indicated a direct relationship between the ability of the receptor to bind to the virus and to neutralize the virus.

Because large-scale production of tmICAM-1 is not presently economically feasible, and because maintenance of tmICAM-1 in an active form requires the use of detergents, alternate means of producing a receptor protein for use as a rhinovirus inhibitor are desirable. Forms of the tmICAM-1 cDNA gene have been developed (as well as cell lines that produce the expression products; U.S. Ser. No. 07/390,662) that have been genetically altered to produce truncated ICAM-1 molecules. See FIG. 2. These truncated forms of ICAM-1 (tICAM(453) and tICAM(185)) lack the transmembrane region and are secreted into the cell culture medium. They bind to rhinovirus in the assay described in Greve, et al., Cell, 56:879 (1989), supra, although at substantially reduced levels relative to tmICAM-1. Thus, their effectiveness as inhibitors of rhinoviral infectivity appeared to be less than that of tmICAM-1. See generally co-pending applications U.S. Ser. No. 07/130,378; U.S. Ser. No. 07/262,570; U.S. Ser. No. 07/239,571; U.S. Ser. No. 07/262,428; U.S. Ser. No. 07/390,662; U.S. Ser. No. 07/678,909; U.S. Ser. No. 07/631,313; U.S. Ser. No. 07/301,192; U.S. Ser. No. 07/449,356.

U.S. Ser. No. 07/239,571 filed Sep. 1, 1988, and its CIP applications U.S. Ser. No. 07/262,428, U.S. Ser. No. 07/390,662 (abandoned in favor of continuation U.S. Ser. No. 07/678,909), and U.S. Ser. No. 07/631,313 are directed to the use of transmembrane rhinovirus receptor as an inhibitor of rhinovirus infectivity using non-ionic detergent to maintain the transmembrane protein in solution, and directed to truncated intercellular adhesion molecules (tICAM) comprising one or more of the extracellular domains I, II, III, IV, and V of tmICAM, which truncated forms do not require the presence of non-ionic detergent for solubilization (see FIG. 2).

U.S. Ser. No. 07/130,378 filed Dec. 8, 1987, and its CIP application U.S. Ser. No. 07/262,570 (now abandoned) are directed to transfected non-human mammalian cell lines which express the major rhinovirus receptor (HRR) and to the identification of HRR as intercellular adhesion molecule.

U.S. Ser. No. 07/301,192, filed Jan. 24, 1989, and its CIP application U.S. Ser. No. 07/449,356 are directed to a naturally-occurring soluble ICAM (sICAM) related to but distinct from tmICAM in that this sICAM lacks the amino acids spanning the transmembrane region and the cytoplasmic region; in addition this sICAM has a novel sequence of 11 amino acids at the C-terminus.

Subsequently, Marlin, S. D., et al., Nature, 344:70 (1990), reported the construction and purification of a truncated soluble form of the normally membrane-bound ICAM-1 molecule which they termed sICAM-1. It has both the transmembrane domain and the cytoplasmic domain of the protein deleted and differs from the wild-type amino acid sequence by a single conservative substitution at its carboxyl end. It is composed of residues 1-452 of ICAM-1 plus a novel phenylalanine residue at the C-terminus. These workers demonstrated that sICAM-1 was required at levels >50 µg/ml to prevent the binding of HRV14 virus to cells. However, they also found that sICAM-1 at 1 µg/ml (18 nM), when continually present in the culture medium, was able to inhibit by 50% the progression of an infection by HRV54. The inhibitory activity was correlated with the receptor class of the virus, in that Coxsackie A13 but not poliovirus or HRV2 was inhibited; infectivity data for HRV14 was not reported, however. Thus, they did not demonstrate a direct correlation between binding and inhibition of infectivity. Further, as discussed in greater detail, infra, attempts to reproduce the results obtained by Marlin, et al. have not been successful.

To date, no one has been able to demonstrate an agent that binds to and effectively reduces infectivity of human rhinovirus (by blocking vital infection with isolated cell surface receptor protein) as effectively as tmICAM-1; accordingly there continues to exist a need in the art for a form of ICAM-1 that can effectively bind to human rhinovirus and can effectively reduce HRV infectivity.

BRIEF SUMMARY OF THE INVENTION

Provided by the invention are multimeric configurations of transmembrane ICAM (tmICAM-1) and multimeric configurations of non-transmembrane ICAMs (tICAMs), having improved rhinovirus binding activity.

As noted, supra, tmICAM-1 isolated from mammalian cells has the capacity to neutralize human rhinoviruses belonging to the major receptor group, but only if maintained in solution with detergent. Certain soluble fragments of ICAM-1 have been found to have a reduced capacity for binding virus and do not reduce infectivity as effectively as tmICAM-1. To date, no one has been able to ascertain the reason for this reduced capacity.

It has been proposed by others that the rhinovirus receptor exists on cells in a pentameric form. Tomassini, J., and Colonno, R., J. Virol., 58:290-295 (1986). However, quantitation (unpublished results of the co-inventors herein) of the rhinovirus and anti-ICAM-1 monoclonal antibody (Mab) binding to HeLa cells has revealed a maximum of 30,000 virions bound per cell (determined by the binding of [$^{35}$S] methionine-labeled HRV) and 50,000-60,000 ICAM-1 molecules per cell (determined by the binding of radio-labeled Mab to ICAM-1). These results prompted further studies to examine the possibility that rather than five, only between one and two ICAM-1 molecules on the surface of cells are bound per HRV particle bound to the cell.

Genetically engineered forms of truncated ICAM-1 that lack the C-terminal transmembrane domain are secreted into the culture medium of mammalian cells transfected with the recombinant gene. The purification of such secreted ICAM molecules from spent culture medium of cells stably transfected with the genes therefor is described herein. In a solution-HRV binding assay and in an HRV neutralization assay, it was found that the monomeric forms tend to have substantially reduced avidity for HRV relative to tmICAM-1. However, it has now been discovered that when such tICAMs are presented in multimeric form and then incubated with HRV, the virus-binding activity of the multimeric tICAMs becomes comparable to that of tmICAM-1. This binding of multimeric tICAMs to HRV has the same properties as the binding of HRV to ICAM-1 on HeLa cells: it is inhibited by anti-ICAM-1 Mabs, it is specific for rhinoviruses of the major receptor group, and has the same temperature dependence as the binding of rhinovirus to cells (i.e., binds well at 37° C. and undetectably at 4° C.). It is postulated that tmICAM exists in nature in a multimeric, possibly dimeric form, and that such constructs more closely resemble the native configuration, with its attendant high avidity for the human rhinovirus. Such dimerization may conveniently be achieved in vitro by, e.g., crosslinking two ICAM monomers by chemical means or by crosslinking with appropriate antibodies, or by binding monomers to appropriate inert substrates. Multimerization can also be achieved in vivo by modification of the gene sequence coding for the select ICAM to provide appropriate binding sites in the corresponding peptide sequence. For example, muteins can be engineered which contain appropriate cysteine residues to allow in vivo multimerization via interchain disulfide bonding. Alternatively, a DNA sequence coding for an ICAM may be fused with a DNA sequence coding for an appropriate immunoglobulin or fragment thereof, such that the fusion gene product possesses at least one site suitable for interchain bonding. The resulting fusion peptide monomer can then be expressed by the cell in multimeric form. Under certain circumstances, the benefits of multimerization may also be achieved by construction of ICAM muteins containing multiple rhinovirus binding sites.

Also provided by the invention are methods for enhancing binding of ICAM and functional derivatives thereof to a ligand, i.e., human rhinovirus, and "major" group receptor viruses, lymphocyte function-associated antigen-1 (LFA-1), *Plasmodium falciparum* (malaria) and the like, wherein the ICAM is presented in a multimeric configuration to the ligand to facilitate binding of the ICAM to the ligand.

Also provided by the invention are novel pharmaceutical compositions comprising a pharmaceutically acceptable solvent, diluent, adjuvant or carrier, and as the active ingredient, an effective amount of a polypeptide characterized by having human rhinovirus binding activity and reduction of virus infectivity. Dimeric configurations of ICAM and fragments thereof are presently preferred.

Other aspects and advantages of the present invention will be apparent upon consideration of the following detailed description thereof which includes numerous illustrative examples of the practice of the invention.

DESCRIPTION OF THE FIGURES

FIG. 1 shows the protein Sequence of tmICAM-1.

FIGS. 2A, B, C, D and E, F are schematic renditions of tmICAM-1 (FIG. 2A), tICAM(453) (FIG. 2B), tICAM(283) (FIG. 2C), tICAM(185) (FIG. 2D), and tICAM(88) (FIG. 2E). Crosshatch indicates signal region; shaded indicates transmembrane region.

FIGS. 3A, B, C, D and E are schematic diagrams of the constructs of Example 12: FIG. 3a) the heavy chain of human IgG; FIG. 3b) the fragment of the heavy chain used in making the immunoadhesin; FIG. 3c) the fragment of ICAM; FIG. 3d) the completed IgG/ICAM immunoadhesin monomer; FIG. 3e) dimerized configuration.

FIGS. 4A, B and C show crosslinking of tICAM(453) into dimers by water-soluble carbodiimide/N-hydroxysuccinimide. tICAM(453) at the indicated concentrations was crosslinked with 100 mM EDC/5 mM NHS at pH 7.5 for 18 hr at 20 C. The samples were analyzed by SDS-PAGE followed by western blotting with anti-ICAM-1 antisera. FIG. 4a) western blot of crosslinked ICAM(453) showing monomer and dimer species; FIG. 4b) dependence of crosslinking upon tICAM(453) concentration; FIG. 4c) the crosslinking of tICAM(453) is not inhibited by an excess of third-party proteins.

FIG. 5a) tmICAM-1 (crosshatch indicates signal region, shaded indicates transmembrane region)

FIGS. 6A, B, C and D show uncoating of HRV by tICAM(453) over 24 hours. FIG. 6a) shift from native 148S form to uncoated 42S form by tICAM(453); FIG. 6b) shift from native 148S to uncoated 42S form by tICAM(185)

FIG. 7 shows the predicted alignment of ICAM-1 amino acid sequence in domains IV and V onto the immunoglobulin fold motif. Arrows indicate beta strands, pointing from the N- to the C-terminus; italicized letters in bold indicate the beta strands, and numbered residues indicate cysteine residues with disulfide bonds indicated by lines. The dotted line divides the "B" and "F" faces of the domains. Residues indicated with an * are among those replaced with cysteine residues.

DETAILED DESCRIPTION OF THE INVENTION

Figure 5A:
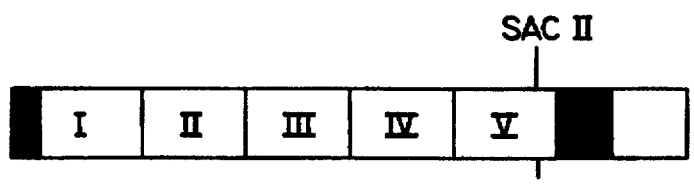
FIGS. 5A, B, C, D and E are schematics showing construction of tICAM(1–451)/LFA-3(210–237) chimera.
Figure 5B:
FIG. 5b) tICAM(1–451)
Figure 5C:
FIG. 5c) LFA-3.
Figure 5D:
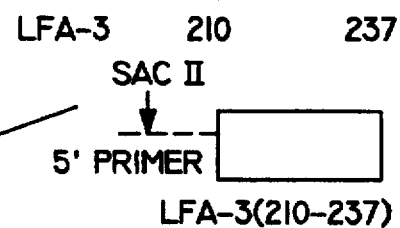
FIG. 5d) LFA-3(210–237)
Figure 5E:
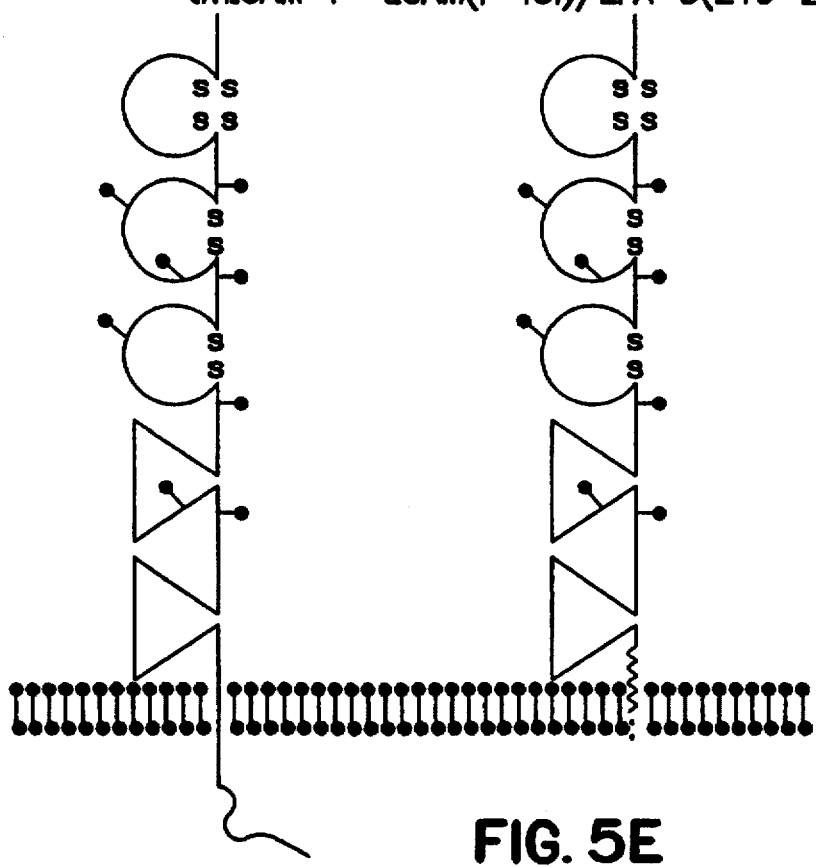
FIG. 5e) tICAM (1–451)/LFA-3(210–237) chimera; structure of tmICAM-1 shown for comparison.

As used herein, the following abbreviations and terms include, but are not necessarily limited to, the following definitions.

| Abbreviation | Definition |
| --- | --- |
| ICAM | Intercellular adhesion molecule-may be used to denote both full length (transmembrane) and truncated (non-transmembrane) forms of the protein. |
| ICAM-1 | Intercellular adhesion molecule-1, also known as tmICAM-1 and HRR; denoting the full-length transmembrane protein |
| tmICAM-1 | Transmembrane intercellular adhesion molecular-1, also known as ICAM-1 and HRR; requires, e.g., detergent conditions to be solubilized |
| HRR | Human rhinovirus receptor, also known as ICAM-1 and tmICAM-1 |
| sICAM-1 | A naturally-occurring soluble truncated form of ICAM-1 having both the hydrophobic transmembrane domain and the carboxy-terminal cytoplasmic domain of ICAM-1 deleted: consists of amino acids 1-442 of ICAM-1 plus 11 novel amino acids; distinguishable from Staunton, et al. tICAM453 which consists of amino acids 1-453 with the terminal tyrosine replaced with phenylalanine. |
| tICAMs | Truncated intercellular adhesion molecules; soluble non-transmembrane ICAMs lacking the hydrophobic transmembrane domain and the carboxy-terminal cytoplasmic domain of ICAM-1. |
| tICAM(1–453) tICAM-453 tICAM(453) | Truncated form of ICAM comprising the entire extracellular amino-terminal domain of tmICAM (domains I–V, amino acid residues 1–453) |
| tICAM(1–283) tICAM-283 tICAM(283) | Truncated form of ICAM comprising domains I, II, and III (amino acid residues 1–283) |
| tICAM(1–185) tICAM-185 tICAM(185) | Truncated form of ICAM comprising domains I and II (amino acid residues 1–185) |
| tICAM(1–88) tICAM-88 tICAM(88) | Truncated form of ICAM comprising domain I (amino acid residues 1–88) |
| tICAM(89–185) | Truncated form of ICAM comprising domain II (amino acid residues 89–185) |
| tICAM(186–283) | Truncated form of ICAM comprising domain III (amino acid residues 186–283) |
| tICAM(284–385) | Truncated form of ICAM comprising domain IV (amino acid residues 284–385) |
| tICAM(286–453) | Truncated form of ICAM comprising domain V (amino acid residues 386–453) |
| tICAM(75–77) | Truncated form of ICAM comprising amino acid residues 75–77 |
| tICAM(70–72) | Truncated form of ICAM comprising amino acid residues 70–72 |
| tICAM(64–66) | Truncated form of ICAM comprising amino acid residues 64–66 |
| tICAM(40–43) | Truncated form of ICAM comprising amino acid residues 40–43 |
| tICAM(36–38) | Truncated form of ICAM comprising amino acid residues 36–38 |
| tICAM(30–33) | Truncated form of ICAM comprising amino acid residues 30–33 |
| tICAM(26–29) | Truncated form of ICAM comprising amino acid residues 26–29 |

The foregoing terms defining specific fragments are intended to include functional derivatives and analogs thereof. Persons skilled in the art will understand that the given boundaries may vary by a few amino acid residues without affecting the function of the given fragment.

"Multimerization" and "multimeric" include, but are not limited to dimerization and dimeric, and include any multimeric configuration of the ICAM-1 molecule, or fragment thereof, that is effective in reducing viral binding and infectivity.

"Transmembrane" generally means forms of the ICAM-1 protein molecule which possess a hydrophobic membrane-spanning sequence and which are membrane-bound.

"Non-transmembrane" generally means soluble forms of the ICAM-1 protein including truncated forms of the protein that, rather than being membrane-bound, are secreted into the cell culture medium as soluble proteins, as well as transmembrane forms that have been solubilized from cell membranes by lysing cells in non-ionic detergent.

"Truncated" generally includes any protein form that is less than the full length transmembrane form of ICAM.

"Immunoadhesin" means a construct comprising all or a part of a protein or peptide fused to an immunoglobulin fragment, preferably a fragment comprising at least one constant region of an immunoglobulin heavy chain.

"Form" is generally used herein to distinguish among full length and partial length ICAM forms; whereas "configuration" is generally used to distinguish among monomeric, dimeric, and multimeric configurations of possible ICAM forms.

All forms and configurations of the ICAM-1 molecule, whether full length or a fragment thereof, including muteins and immunoadhesins, whether monomeric or multimeric, may be fully or partially glycosylated, or completely unglycosylated, as long as the molecule remains effective in reducing viral binding and infectivity.

"Ligand" is generally used herein to include anything capable of binding to at least one of any of the forms and configurations of ICAM and includes, but is not limited to, human rhinovirus, other viruses that bind to the "major" group human rhinovirus receptor, lymphocyte function-associated antigen-1, and Plasmodium falciparum (malaria).

"Human rhinovirus" generally includes all human serotypes of human rhinovirus as catalogued in Hamparian, V., et al., Virol., 159:191-192 (1987).

The sequence of amino acid residues in a peptide is designated in accordance with standard nomenclature such as that given in Lehninger's Biochemistry (Worth Publishers, New York, 1970).

Full-length ICAM-1, also known as human rhinovirus receptor (HRR), is termed transmembrane ICAM(tmICAM-1). Non-transmembrane ICAMs are also known as truncated ICAMs, i.e, ICAMs substantially without the carboxyl intracellular domain and without the hydrophobic membrane domain of tmICAM, which are soluble without the addition of detergent. tICAMs may conveniently comprise one or more domains selected substantially from domains I, II, III, IV, and V of the extracellular region of tmICAM. tICAMs may also comprise functional analogs of tmICAM or fragments thereof, and may also comprise one or more fragments of tmICAM spliced together, with or without intervening non-tmICAM linking sequences, and not necessarily in the same order found in native tmICAM. Presently preferred tICAMs include but are not limited to forms tICAM(453), tICAM(185), tICAM(88), tICAM(283), and tICAMs comprising one or more sequences selected from tICAM(89-185), tICAM186-283, tICAM(284-385), tICAM(386-453), tICAM(75-77), tICAM(70-72), tICAM (64-66), tICAM(40-43), tICAM(36-38), tICAM(30-33), and tICAM(26-29). See U.S. Ser. No. 07/631,313 and U.S. Ser. No. 07/678,909. Non-transmembrane forms of ICAM can include functional derivatives of ICAM, mutein forms of tICAM to facilitate coupling, and tICAM immunoadhesins. When the tICAMs are in a multimeric configuration, preferably as dimers, they display enhanced binding of human rhinovirus and are able to reduce viral infectivity.

Multimerization can be achieved by crosslinking a first ICAM to a second ICAM, using suitable crosslinking agents, e.g. heterobifunctional and homobifunctional crosslinking reagents such as bifunctional N-hydroxysuccinimide esters, imidoesters, or bis-maleimidohexanes.

The different forms of ICAM, transmembrane and non-transmembrane, can be multimerized by adsorption to a support. This support can be made of materials such as nitrocellulose, PVDF, DEAE, lipid polymers, as well as amino dextran, or a variety of inert polymers that can adsorb or can be coupled to tICAM, either with-or without a spacer or linker.

Multimeric ICAM can also be multimerized by coupling the ICAM to a member, e.g., an antibody that does not interfere with HRV binding, or fragments thereof; or to a protein carrier. An example of an antibody includes anti-ICAM antibody CL 203 or a fragment thereof; suitable protein carriers include albumin and proteoglycans.

To facilitate coupling, the ICAM can be modified with at least one reactive amino acid residue such as lysine, cysteine, or other amino acid residue(s) to provide a site(s) to facilitate coupling. These types of modified ICAM are referred to as muteins. The nucleotide sequence for the ICAM of the method can be contained in a vector, such as a plasmid, and the vector can be introduced into a host cell, for example eukaryotic or prokaryotic cells. The preferred eukaryotic cell is a mammalian cell, e.g. Chinese hamster ovary cells or HEK293S cells; the preferred prokaryotic cell is E. coli. In addition, the ICAM can be modified at either terminus to comprise a lipid capable of promoting formation of oligomer micelles. The ICAM comprising the multimeric ICAM can be either fully glycosylated, partially glycosylated, or non-glycosylated.

A preferred manner of making multimeric forms of ICAM-1 is by engineering of cysteine residues into the tICAM sequence (tICAM(453) is particularly preferred) in a position at or close to the natural site of self-association on ICAM-1 monomers. Muteins with cysteine residues placed at appropriate positions form covalent bonds (disulfide bonds) that stabilize an interaction which is noncovalent in vivo. Such muteins are assembled intracellularly and are expressed as a disulfide-linked dimer; alternatively, monomeric muteins may be crosslinked in vitro by incubation at high protein concentration in mildly reducing conditions to encourage disulfide exchange, or by crosslinking with bifunctional chemical crosslinking reagents which react with free sulfhydryl groups. Another advantage of such proteins is that any novel amino acids engineered into ICAM-1 are hidden on the dimer interface and would be less likely to be immunogenic.

In another preferred embodiment, ICAM can also be multimerized by fusion with fragments of immunoglobulins to form ICAM immunoadhesins. For example, an ICAM or fragment thereof can be fused with a heavy or light chain immunoglobulin or fragment thereof, in particular with the constant region of the heavy chain of IgG, IgA, or IgM. Preferably, the constant region contains the hinge region and one or more of CH2 and CH3, but does not contain CH1. The variable region (Fab) of the immunoglobulin is thus replaced by the ICAM or fragment thereof. Such constructs are conveniently produced by construction and expression of a suitable fusion gene in a suitable expression system [see, e.g., Bebbington, C. R. and C. C. G. Hentschel, "The use of vectors based on gene amplification for the expression of cloned genes in mammalian cells," in DNA Cloning, Vol. III, D. Glover, ed.(1987)] and are secreted in a dimerized configuration.

Also provided by the invention are methods for enhancing binding of ICAM and functional derivatives thereof to a ligand, i.e., human rhinovirus, and "maJor" group receptor viruses, lymphocyte function-associated antigen-1 (LFA-1), *Plasmodium falciparum* (malaria) and the like, wherein the ICAM is presented in a multimeric configuration to the ligand to facilitate binding of the ICAM to the ligand.

Also provided by the invention are novel pharmaceutical compositions comprising a pharmaceutically acceptable solvent, diluent, adjuvant or carrier, and as the active ingredient, an effective amount of a polypeptide characterized by having human rhinovirus binding activity and reduction of virus infectivity. Dimeric configurations of ICAM and fragments thereof are presently preferred.

The following examples illustrate practice of the invention.

Example 1 relates to growth, purification and assay of rhinoviruses;

Example 2 relates to production and isolation of monoclonal antibodies to ICAM-1;

Example 3 relates to construction of non-transmembrane truncated forms of ICAM cDNA from full length ICAM-1 cDNA;

Example 4 relates to transfection of mammalian-cells and expression of non-transmembrane truncated forms of ICAM cDNA;

Example 5 relates to isolation and purification of non-transmembrane truncated forms of ICAM-1;

Example 6 relates to radioactive labeling of tmICAM-1, tICAM(185), and tICAM(453) and demonstration of retained capacity for binding to monoclonal antibodies;

Example 7 relates to human rhino-virus binding assays of transmembrane and of transmembrane truncated forms of ICAM-1;

Example 8 relates to CL203 IgG antibody-mediated cross-linking of tICAM(453);

Example 9 relates to multimerization of transmembrane and of non-transmembrane truncated forms of ICAM-1;

Example 10 relates to infectivity-neutralization assay of multimeric transmembrane and of multimeric non-transmembrane truncated forms of ICAM-1; and Example 11 relates to use of multimeric forms of transmembrane and truncated forms of ICAM-1, as effective inhibitors of ICAM/LFA-1 interaction.

Example 12 relates to construction of a tICAM(185)/IgG immunoadhesin.

Example 13 relates to efficient rhinovirus binding and neutralization by a tICAM(185)/IgG immunoadhesin.

Example 14 relates to in vitro dimerization of ICAM-1.

Example 15 relates to a tICAM(1–451)/LFA-3(210–237) chimera.

Example 16 relates to irreversible inactivation of HRV by ICAM.

Example 17 relates to cysteine muteins.

EXAMPLE 1

Growth, Purification and Assay of Rhinoviruses

Rhinoviruses were grown, purified, and assayed essentially as described in Abraham, G., et al., J. Virol., 51:340 (1984) and Greve, et al., Cell, 56:839 (1989). The serotypes chosen for these studies include HRV14, the standard in the field, and HRV3, which has an approximately 10-fold higher affinity for ICAM than does HRV14. HRV2, which binds to the "minor" receptor rather than the "major" receptor, was used as a negative control.

Rhinoviruses HRV2, HRV3, and HRV14 were obtained from the American Type Culture Collection, plaque purified, and isolated from lysates of infected HeLa-S3 cells. Purified rhinovirus was prepared by polyethylene glycol precipitation and sucrose gradient sedimentation. Viral purity was assessed by SDS-PAGE analysis of capsid proteins and by electron microscopy. Infectivity was quantitated by a limiting dilution infectivity assay scoring for cytophathic effect, essentially as described by Minor, P. D., Growth, assay and purification of picornaviruses, in *Virology:A Practical Approach*, B. W. J. Mahy, ed (Oxford:IRL Press), pp. 25–41.

EXAMPLE 2

Production and Isolation of Monoclonal Antibodies to ICAM-1

BALB/cByJ female mice were immunized by intraperitoneal injection of 107 intact HeLa cells in 0.5 ml of phosphate-buffered saline (PBS) three times at 3-week intervals. Two weeks later the mice were bled and aliquots of serum were tested for protective effects against HRV14 infection of HeLa cells. Positive mice were boosted by a final injection of $10^7$ HeLa cells, and 3 days later spleen cells were fused to P3X63-Ag8.653 myeloma cells (Galfre, et al., Nature, 266:550–552 (1977)) to produce a total of approximately 700 hybridoma-containing wells. Each well was tested by incubating $3\times10^4$ HeLa cells in 96-well plates with 100 μl of supernatant for 1 hr at 37 C; the cells were then washed with PBS, and a sufficient amount of HRV14 was added to give complete cytopathic effect in 24–36 hr. Wells that were positive (protected from infection) were scored at 36 hr.

Cells were removed from wells which scored positive in the first screen and cloned by limiting dilution in 96-well microtiter plates. Supernatants from these wells were tested in the cell protection assay and positive wells were again identified. Further clonings were performed until all of the hybridoma containing wells were positive indicating a clonal population had been obtained. Four cloned cell lines, and their corresponding antibodies, were obtained and were designated c78.1A, c78.2A, c78.4A, c78.5A, c92.1A and c92.5A, respectively.

C92.1A was deposited on Nov. 19, 1987 with the American Type Culture Collection, 12301 Parklawn Drive, Rockville, Md. 20852 and was designated HB 9594.

EXAMPLE 3

Construction of tICAM cDNAs From Full Length ICAM-1 cDNA

A. Preparation of ICAM-1 cDNA

Randomly-primed cDNA was synthesized from poly A+ RNA from HE1 cells using an Amersham(TM) cDNA synthesis kit under conditions recommended by the supplier. PCR amplification was performed using 100 ng of cDNA for 25 cycles using primers PCR 5.1: (ggaattcATGGCTCCCAGCAGCCCCCGGCCC) and PCR 3.1: (ggaattcTCAGGGAGGCGTGGCTTGTGTGTT). Amplification cycles consisted of 94 C 1 min, 55 C 2 min, and 72 C 4 min. The product of the PCR reaction was digested with EcoR1 and cloned with EcoR1 digested phage vector lambdaGT10 (Stratagene(TM)). Recombinant phage clones were screened by plaque hybridization using ICAM-1 specific oligonucleotides GAGGTGTTCTCAAA-CAGCTCCAGCCCTTGGGGCCGCAGGTCCAGTTC (ICAM1) and CGCTGGCAGGACAAAGGTCTG-GAGCTGGTAGGGGGCCGAGGTGTTCT (ICAM3).

A positive clone designated lambdaHRR4 was selected and purified. The insert was removed by EcoR1 digestion and subcloned into the EcoR1 site of Bluescript KS+. This clone was designated pHRR2. The entire insert was sequenced and found to contain the entire ICAM-1 coding sequence beginning with the initiator ATG codon and ending with the TGA stop codon as specified by the PCR ICAM-1 sequence (Simmons, et al., Nature, 331:624 (1988); Staunton, et al., Cell, 52:925–933 (1988)) by a single substitution of Ala-1462 for Gly. This same change was identified in several independent clones and thus represents a polymorphism of the ICAM-1 gene.

B. Construction of tICAM(453) and tICAM(185)

Modified forms of the ICAM-1 cDNA were created by PCR amplification reactions (Saiki, et al., Science, 230:1350–1354 (1985)) using the full length ICAM-1 cDNA clone pHRR-2 as template. The plasmid DNA was digested with EcoR1 to excise the ICAM-1 insert and treated with alkaline phosphatase to prevent re-circularization of the vector in subsequent ligation steps. Ten ng of template DNA was subjected to 10 cycles of PCR amplification using oligonucleotide primers PCR5.5 and PCR3.3 for tICAM-453 and PCR5.5 and 3.10 for tICAM-185 under the following conditions:

| Temperature (°C.) | Time (mins) |
| --- | --- |
| 94 | 1 |
| 55 | 2 |
| 72 | 1.5 |
| 71 | 4 (final extension) |

PCR5.5 has the sequence: GGAATTCAAGCTTCT-CAGCCTCGCTATGGCTCCCAGCAGCCCCCGGCCC which consists of EcoR1 and HindIII sites, 12 bp ICAM-1 5' untranslated sequence, and the first 24 bp encoding the signal peptide.

PCR3.3 has the sequence: GGAATTCCTGCAGTCACT-CATACCGGGGGGAGAGCACATT which consists of EcoR1 and Pst1 sites, a stop codon, and 24 bp complementary to the bases encoding the last 8 extracellular amino acids of ICAM-1 (residues 446–453).

PCR3.10 has the sequence: TTCTAGAGGATCCT-CAAAAGGTCTGGAGCTGGTAGGGGG which consists of Xba1 and BamH1 sites, a stop codon, and 24 bp complementary to the bases encoding residues 178–185 of ICAM-1.

The PCR reaction products were digested with EcoR1 (tICAM(453)) or EcoR1 and BamH1 (tICAM(185)) and cloned into the polylinker site of Bluescript SK+ (Stratagene). Clones containing the desired inserts were verified by restriction analysis and DNA sequencing. The inserts were excised from Bluescript by digestion with HindIII and XbaI and inserted into the expression vector CDM8 (Seed, Nature, 239:840 (1987) at the HindIII and XbaI sites. A clone containing the tICAM(453) insert designated pHRR-8.2 and a clone containing the tICAM(185) insert designated pHRR23–13 were selected and subjected to extensive sequence analysis. This verified the existence of the desired stop codons, and the integrity of the selected regions of ICAM-1 coding sequence.

These plasmids were transfected into COS cells using the DEAE-dextran techniques and the cells were cultured 72 hr. before assay. Surface expression was monitored by FACS using indirect immunofluorescence and a monoclonal antibody specific for ICAM-1. Transient expression in COS cells and immunoprecipitation of metabolically labelled ([$^{35}$S]cysteine) cell supernatants with c78.4A Mab (monoclonal antibody) demonstrated the production of soluble ICAM-1 fragments of 45 kd and 80 kd from pHRR23-13 and pHRR8.2, respectively. The preparation of stable Chinese hamster ovary cell transfectants is described below in Example 4.

C. Modified Non-glycosylated tICAM-1

A modified full length ICAM-1 was made by simultaneous mutagenesis of Asn at positions 103, 118, 156 and 173 each to Gln. This removes all four Asn-linked glycosylation sites from extracellular domain II of the ICAM-1 molecule. The resultant molecule, referred to as non-glycosylated transmembrane ICAM, was expressed on the surface of COS cells and was able to bind radio-labeled HRV3 at levels comparable to unmodified ICAM-1. This result demonstrated that glycosylation of domain II (the first 185 amino acids) is not required for virus binding to ICAM-1.

It is expected that non-transmembrane ICAM can be similarly modified to yield modified non-glycosylated non-transmembrane ICAM-1 molecules.

D. Construction of Genetically Engineered Forms of tICAM Containing Reactive Residues Suitable for Cross-Linking to Form Multimers A molecule consisting of the 453 amino acid extracellular domain of ICAM-1 with the addition of a novel lysine residue at the C-terminus was constructed by PCR modification of the pHRR-2 cDNA described in Example 3B. The primers used were PCR5.5 (Example 3B) and PCR 3.19 which has the sequence: TTCTAGAGGATCCTCACTTCT-CATACCGGGGGGAGAGCACATT and consists of XbaI and BamHI sites, a stop codon, a Lys codon, and 24 bases complementary to the sequence encoding amino acid residues 446 to 453. Following cloning into the CDM8 vector, production of tICAM having a Lys at position 453 was confirmed by transient expression in COS cells. Stable CHO cell lines were generated by co-transfection with pSV2-DHFR as described in Example 4. The same strategy was used to add a Lys residue to the C-terminus of tICAM(185) using PCR5.5 and PCR3.20 which has the sequence: TTCTAGAGGATCCTCACTTAAAGGTCTG-GAGCTGGTAGGGGGC and consists of XbaI and BamHI sites, a stop codon, a Lys codon, and 24 bases complementary to the sequence encoding residues 178 to 185. Transient COS cell expression confirmed the production of tICAM-185 and stable CHO cell lines were derived as described in Example 4.

Three modified forms of tICAM(452) that each contain an additional Cys residue were constructed by site-directed mutagenesis of the full-length ICAM-1 cDNA. In each construct a stop codon was introduced by changing the Glu residue at position 453 from GAG to TAG. The C-terminus is thus Tyr-452. Residues Asn-338, Thr-360, and Gln-387 were each separately mutated to Cys using a second site directed mutagenesis. The presence of the desired mutations were confirmed by DNA sequencing.

The residues selected for mutation to Cys were selected based on a computer generated plot of surface probability which predicts surface exposure of these regions. Also, Thr-360 is in close proximity to Asn-358 which is a site of potential Asn-linked glycosylation. Each of the three Cys mutants was expressed and secreted into the medium of transfected COS cells. Examination of the proteins under reducing and non-reducing conditions showed no indication of the presence of dimers. It is anticipated that cross-linking reagents reactive with sulfhydryl groups can be used to cross-link the Cys-modified tICAM forms to obtain multimeric forms.

EXAMPLE 4

Transfection of Cells and Expression of tICAM cDNA

A. Transfection of Eukaryotic Cells

Chinese hamster ovary (CHO) cells deficient in dihydrofolate reductase (DHFR) were obtained from Cutter Labs (Berkeley, Calif.). DHFR- cells cannot synthesize nucleosides and therefore require a nucleoside-supplemented medium. The cells were co-transfected with the plasmid pSV2-DHFR which contains the mouse dihydrofolate reductase (DHFR) gene under control of the SV40 promoter, and with tICAM(453), or tICAM(184) constructs in the CDM8 vector (Seed and Aruffo, PNAS, 84:3365–3369 (1987)).

Transfections were done using both electroporation and calcium phosphate methods. Bebbington, supra. Transfected DHFR-positive cells were selected by growth on nucleoside-free media, and pools of transfectants were cloned by limiting dilution.

Cell lines that secrete tICAM were identified by testing culture supernatants with a two-site radioimmune assay (RIA) for ICAM using Mabs c78.4A and c78.5A as follows. A monoclonal antibody against one epitope on ICAM (for example, Mab c78.4A) was adsorbed to plastic 96-well plates (Immunlon plates, Dynatech Inc.), excess binding sites on the plates were blocked with bovine serum albumin (BSA), and then culture supernatants were incubated with the plates. The plates were washed and incubated with 125I-Mab (directed against a second epitope on ICAM, e.g. c78.5A), and, after washing, the amount of bound 125I-IgG determined. The concentration of tICAM was determined by comparing RIA data from unknowns against a standard curve of tmICAM at known concentrations. Positive clones were expanded and expression of tICAM forms was confirmed by immunoprecipitation of metabolically labeled cell supernatants with Mab c78.4A.

Cell lines CT.2A (tICAM(453)) and CD12.1A (tICAM (185)) were selected for further study and were subjected to gene amplification in methotrexate containing media as described by Bebbington, et al., supra. A clone derived from CT.2A resistant to 100 nM methotrexate and a CD12.1A clone resistant to 1 µM methotrexate were used for purification of soluble truncated ICAM-1 proteins.

B. Transfection of Prokaryotic Cells

Because glycosylation of the viral binding domain of ICAM is not required to retain viral binding (as demonstrated in Example 3C), it is anticipated that prokaryotic cells, such as E. coli, can be successfully transfected to produce functional proteins.

EXAMPLE 5

Isolation and Purification of tICAM-1

Monoclonal antibody affinity chromatography with c78.4A-Sepharose(TM) has been previously described in co-pending U.S. Ser. No. 07/130,378 and Greve, et al., Cell, 56:839–847 (1989). tICAM secreted into serum-containing media required additional purification steps due to the high level of contaminating protein in the serum. Before elution from the Mab-affinity column, the column was washed with 1M NaCl to remove loosely-bound proteins. For tICAM (453), the partially purified tICAM(453) eluted from the c78.4-Sepharose(TM) column was dialyzed into 10 mM Tris (pH 6.0), absorbed onto a mono-Q(TM) column (Pharmacia), and eluted with a 0–0.3M NaCl gradient. tICAM184 was further purified by gel filtration on a Superose-12(TM) column.

It is also recognized that non-transmembrane truncated forms of ICAM-1 may be purified using standard ion exchange methodology without using monoclonal antibody affinity chromotography.

EXAMPLE 6

Radioactive Labeling of tmICAM-1, tICAM(185), and tICAM(453) and Demonstration of Retained Capacity for Binding to Monoclonal Antibodies The epitopes reactive with monoclonal antibodies c78.4A and c78.5A are conformationally-dependent epitopes and thus can be used as analytical probes for confirming retention of the native ICAM structure. Known amounts of purified ICAM were incubated with c78.4A or c78.5A IgG-Sepharose(TM) and the fraction of the radioactivity bound determined. These experiments showed that the purified tmICAM-1, tICAM(185), and tICAM(453) completely retained the ability to bind to these monoclonal antibodies.

Transfectants were metabolically labeled with [$^{35}$S] cysteine, and cell lysates (for transmembrane ICAM) or culture supernatants (for truncated ICAM) were prepared and incubated with c78.4A IgG-Sepharose(TM) beads. The beads were washed and adsorbed proteins were eluted with sodium dodecyl sulfate (SDS) and analysed by SDS-PAGE; see Greve, et al., Cell, 56:839–847 (1989)). It was found that the isolated proteins were quantitatively bound to the c78.4A and c78.5A Mabs.

Accordingly, the tICAM(185) and tICAM(453) both have retained native ICAM structure.

EXAMPLE 7

Human Rhinovirus Binding Assays of tmICAM and tICAMs

Described below are three binding assays used to assess binding activity of the various forms of ICAM.

A. Pelleting Assay

[$^{35}$S]cysteine-labeled tmICAM-1 or tICAM was mixed with HRV3 in 100 µl of 10 mM HEPES (pH 7.5), 150 mM NaCl, 1 mM $MgCl_2$, 1 mM $CaCl_2$, 0.1% Triton X-100. The mixture was incubated for 30 min. at 37 C, cooled on ice, layered on top of a cushion of 200 µl of 10% glycerol, 0.2M triethanolamine (pH 7.5), and centrifuged in a Beckman air-driven centrifuge at 134,000×g for 30 min. at 4 C. The top 275 µl was removed, and the pellet was analyzed by SDS-PAGE and scintillation counting. Silver-staining of SDS gels of control experiments indicated that essentially all of the HRV3 is pelleted under these conditions and essentially all of the ICAM remains in the supernatant. The results are shown in Table 1.

TABLE 1

| ICAM | % ICAM Pelleted* |
|---|---|
| tmICAM-1 | 11.6% |
| tICAM(453) | 1.0% |
| tICAM(185) | 4.3% |

*average of 4 experiments: these numbers cannot be directly converted into relative affinities These data show that both truncated forms of ICAM bind to rhinovirus, but at substantially reduced levels relative to tmICAM.

B. Solution Binding Assay

To obtain quantitative information on the relative affinity of tmICAM and tICAM fragments in solution, a solution competition assay was developed in which soluble tmICAM or soluble tICAM fragments were used to inhibit the binding of [$^{35}$S]HRV3 to previously immobilized ICAM-1; nonionic detergent (Triton X-100) was included in the buffers so that the different proteins could be compared under identical conditions. First, tmICAM-1 (isolated in the presence of 0.1% octylglucoside instead of Triton X-100) was diluted 10-fold into a Tris/NaCl buffer and allowed to adsorb to the walls of a microtiter plate (Immunlon-4, Dynatech) overnight. Nonspecific binding sites on the plate were then blocked with 10 mg/ml BSA and binding experiments performed in 0.1% Triton X-100/1 mg/ml BSA/10 mM Tris/200 mM NaCl. Approximately 20,000 cpm of [$^{35}$S] HRV3 were mixed with varying amounts of ICAM [tmICAM, tICAM(453) or tICAM(185)], incubated for 1 hour at 37 C, and then added to wells of the microtiter plates and incubated for 3 hr at 37 C. The plates were washed and the bound radioactivity determined.

As shown in Table 2, tmICAM-1 inhibits virus binding half-maximally at low concentrations (0.008 µM) while tICAM(453) and tICAM(185) inhibit at much higher concentrations (2.8 µM and 7.9 µM, respectively; or 350 to almost 1000-fold higher than tmICAM.

TABLE 2

| ICAM | IC50* |
|---|---|
| tmICAM | 8.0 ± 3.3 nM (N = 3) |
| tICAM(453) | 2.8 ± 0.6 µM (N = 3) |
| tICAM(185) | 7.9 ± 2.8 µM (N = 3) |

*IC50 is the concentration of soluble ICAM needed to inhibit HRV3 binding by 50%.

These data confirm and extend the earlier observations that tICAM(453) and tICAM(185) do bind to rhinovirus but with lower affinities than does tmICAM-1 and provide evidence that the virus binding site is encompassed within the two N-terminal domains (185 residues) of ICAM-1.

Subsequent experiments performed at 34 C (the temperature at which rhinovirus normally replicates) have yielded similar results.

C. Dot-Blot Assay

An alternative method of measuring binding activity was utilized in which tmICAM-1, tICAM(453), or tICAM(185) was adsorbed to nitrocellulose filters, the non-specific binding sites on the filters blocked with 10 mg/ml bovine serum albumin (BSA), and radioactive virus or [$^{125}$I]Mab to ICAM-1 incubated with the filter for 60 min at 37 C. The filters were washed with buffer and the filters exposed to X-ray film.

The amount of radioactivity bound to the filters was determined by densitometry of the autoradiograms, and the data is expressed as HRV3 binding (in arbitrary units) normalized to the amount of ICAM bound to the blot by a parallel determination of the amount of [$^{125}$I]Mab c78.4A or c78.5A bound to the ICAM (bound to the blot). The results are shown in Table 3.

TABLE 3

| Binding of [$^{35}$S]HRV3 to Immobilized ICAM* | | |
|---|---|---|
| ICAM | tICAM(453) | ratio ICAM/tICAM453 |
| 1.2 ± 1.1 | 0.52 ± 0.45 | 2.3 |

*Average of 5 experiments. Data is expressed in arbitrary densitometric units of [$^{35}$S]HRV3 binding/125I anti-ICAM Mab binding.

Additional studies with tICAM 185 have been performed. Binding experiments have demonstrated equivocal results. It is anticipated that steric hinderance may play a role. The size of the virus is approximately 30 nanometers. The length of tICAM(185) is less than 10 nanomters. The use of a spacer or linker would provide better accessibility for binding.

The results from this experiment indicate that under these assay conditions tICAM(453) is capable of binding rhinovirus at levels comparable to those of tmICAM-1 when the amount of virus bound was normalized to the amount of [$^{125}$I]MAb bound. Further, these results indicate that the tICAM forms are capable of binding to rhinovirus, but that the binding avidity is dependent upon the configuration of the tICAM. tmICAM-1 is believed to be a small multimer (probably a dimer) and presentation of tICAM in a multimeric form mimics this multimeric configuration.

Evidence supporting this hypothesis comes from quantitative binding studies (unpublished), in which the ratio of the maximum number of rhinovirus particles and the maximum number of antibody molecules that can be bound to cells is approximately 1.5, as discussed supra. This is in contrast to the earlier work of Tomassini, J., et al., J. Virol., 58:290 (1986), which suggested a complex of five molecules needed for binding. Their conclusion was based on an erroneous interpretation of gel filtration data that failed to take into account bound detergent molecules.

EXAMPLE 8

CL203 IgG Antibody-Mediated Cross-Linking of tICAM(453)

To provide additional evidence that the higher relative binding activity of tmICAM-1 is due to a multimeric form of the protein, the tICAM(453) protein was pre-incubated with CL203, a monoclonal antibody to ICAM-1 that does not inhibit virus binding to ICAM-1 and binds to a site C-terminal to residue 184 (Staunton, et al., Cell, 56:849 (1989) and Cell, 61:243 (1990)). Thus, the antibody can effectively "cross-link" two molecules of tICAM(453), to create "dimers" of tICAM(453), yet without blocking the virus-binding site on each of the two molecules of tICAM (453). When a mixture of CL203 IgG and tICAM(453) at a 4:1 weight ratio was tested in the competition assay, it was found that the antibody cross-linked tICAM(453) inhibited HRV3 binding at a concentration 7.4-fold lower than tICAM (453) alone consistent with the idea that tmICAM-1 binds with higher affinity to rhinovirus because it is a dimer or a small multimer.

To create alternative multimeric forms of tICAM, several further modified truncated forms of ICAM were constructed as described, supra, in Example 3.

These forms can then be multimerized as described in Example 9, below.

EXAMPLE 9

Multimerization of tmICAM and tICAMs

There are several ways that tICAM can be converted to a multimeric form having enhanced viral binding and neutralization activity over the monomeric form. For example, a first tICAM can be coupled to a second tICAM (which may be the same or different), or to an inert polymer, such as amino-dextran (MW 40,000), using homobifunctional (such as N-hydroxysuccinimide (NHS) esters) or heterobifunctional (such as those containing NHS-ester and photoactivatable or sulfhydryl-reactive groups) cross-linking reagents utilizing the amino group on the amino-dextran and an amino or other group on the tICAM. A number of examples of appropriate cross-linking reagents can be found in the Pierce Chemical Company catalog (Rockford, Ill.). Similarly, the tICAMs can also be bound to other suitable inert polymers, such as nitrocellulose, PVDF, DEAE, lipid polymers, and other inert polymers that can adsorb or be coupled to tICAM, with or without a spacer or linker.

As tICAM is poorly reactive with NHS-ester-based compounds, a tICAM with a genetically-engineered C-terminal lysine residue (see Example 3) would have improved coupling efficiency to supports with homobifunctional reagents, whereas genetically-engineered C-terminal cysteine residues would facilitate coupling by heterobifunctional reagents, such as sulfo-maleimidobenzoyl-N-hydroxysucctnimide ester (MBS).

ICAMs can also be multimerized by coupling with an antibody (e.g. CL203) or fragment thereof, or with a suitable protein carrier, e.g. albumin or proteoglycan.

ICAMs may also be multimerized by fusion with fragments of immunoglobulins to form ICAM immunoadhesins.

Alternatively, soluble tICAM multimers can be created by genetically engineering reactive residues into tICAM. For example, free cysteine residues can be created in relatively hydrophilic sequences in the C-terminal region of tICAM (which would have a greater tendency to be solvent-exposed). This will allow the creation of dimers in situ; alternatively, monomers can be purified and dimers created in vitro by disulfide bonding, either directly or via suitable linkers.

Another approach requires the placement of lysine residues at similar positions and cross-linking purified protein in vitro with homobifunctional NHS-esters. Examples of such lysine residues are residues 338, 360, 387. See FIG. 1.

Crosslinking cysteine residues to each other can be accomplished by reaction of tICAM with free cysteine groups with bis-maleimidohexane (Pierce Chemical Co.) or other bis-maleimido-analogs. Cross-linking free cysteine residues on tICAM to amino groups on carrier molecules can be accomplished by reaction with m-maletmidobenzoyl-N-hydroxysuccinimide ester.

Crosslinking amino groups on tICAM molecules can be accomplished with homobifunctional N-hydroxysuccinimide esters (for examples, see Pierce Chemical Co. catalog). Alternatively, the carbohydrate groups on tICAM can be oxidized to aldehydes and coupled to hydrazine-activated amino groups on a carrier molecule.

EXAMPLE 10

Infectivity-Neutralization Assay of tmICAM and tICAMs

Three different assays for virus infectivity have been used. These different assays take into account the differences in transmembrane ICAM and non-transmembrane solubilities.

A. Plaque-reduction assay in the presence of detergent

The results of this assay indicate the highest dilution of virus that will still be effective in killing cells. Virus is pre-incubated with transmembrane ICAM protein in the presence of 0.1% Triton X100, serially diluted into culture medium, incubated for 30 min with HeLa cells at $10^6$ cells/ml, diluted 10-fold, and plated out into multiple wells of a 96-well microtiter plate having varying dilutions of virus.

0.1% Triton X100 was used as positive control. After 5 days, the wells are scored as either being infected or not by the presence of cytopathic effect (CPE) and the titer expressed as plaque-forming units/ml (PFU/ml) of the original virus. This assay was described in U.S. Ser. No. 07/239,571 and was used to demonstrate the antiviral activity of tmICAM-1 (which required the presence of detergent to remain in solution). The concentration of ICAM protein used is the initial concentration in the pre-incubation mixture; however, the ICAM protein is not present continually during the infection in that the protein is serially diluted. While the presence of detergent is required to solubilize the tmICAM, detergent kills the cells; thus, the need for the serial dilutions of the tmICAM-1/detergent to permit infection of cells.

B. Plaque-reduction assay in the absence of detergent In this plaque-reduction assay, a more traditional assay, HeLa cells are infected with serial dilution of rhinovirus as above, but detergent is not present; thus, this assay cannot be used to assay tmICAM. In this assay the tICAM is present continually in the culture medium at the indicated concentration. tmICAM-1 (which requires the presence of detergent) cannot be assayed in this system because the addition of the required detergent would kill the HeLa cells.

C. Plaque-reduction assay in continual presence of virus and ICAM

This assay is similar to that Utilized by Marlin, et al. (Nature 1990) in which a culture of HeLa cells is infected with 100 PFU of virus in the presence or absence of ICAM protein and cultured approximately 4 days until cytopathic effect (CPE) is apparent. The cultures are then scored for CPE visually. The assay conditions were the same as Marlin, supra. Scoring was done visually rather than by a staining procedure using crystal violet.

In this assay, there is no detergent present, the ICAM is present continually, and this assay measures a reduction in virus replication/propagation at an arbitrary point in time.

The data from these three different assays for virus infectivity is summarized in Table 4.

TABLE 4

| | IC50% (μM)* | | |
|---|---|---|---|
| | Assay: | | |
| ICAM | A | B | C |
| tmICAM-1 | 0.03 | ND | ND |
| tICAM(453) | >20 | 0.2 | 0.2 |
| tICAM(185) | >20 | 8 | ND |

*IC50% is defined as the concentration of ICAM protein needed to inhibit HRV3 infectivity by 50%.

These data indicate that tmICAM-1 is significantly more active in reducing viral infectivity than the truncated ICAM proteins, even when compared in different assay systems. The differences in neutralization activity of tICAM(453) in assay (A) and assay (B) indicate that the neutralization mediated by tICAM(453) requires the continual presence of tICAM(453) in the culture medium and is reversible. That the neutralization is reversible is indicated by the lack of significant neutralization observed in assay (A). In contrast, the neutralization activity of tmICAM-1 is >667-fold higher than tICAM(453) and than tICAM(185) in assay (A) and could be even greater in assay (B) if it were possible to have the tmICAM-1 present continually in the culture medium in the absence of detergent. The conditions in assays B–D more closely reflect the in vivo situation in which soluble ICAM could be used as an antiviral agent.

To compare these results with those of Marlin, et al., an attempt was made to reproduce their assay conditions. As shown in Table 4, there is a good correlation between the results in assay (B) and assay (C), although the IC50% for tICAM(453) is 10-fold greater than that seen by Marlin, et al. To determine if this is due to a difference in the serotype of rhinovirus used, the assay was repeated with HRV14 and HRV54 (the serotype used by Marlin, et al). The IC50% for both of these serotypes was 0.2 µM tICAM(453), indicating that there is no difference in serotype sensitivity between HRV14, HRV54, and HRV3.

To attempt to resolve this discrepancy, the same buffers that Marlin, et al. used were used to see if they affected the infectivity of rhinovirus in assay (C). Marlin, et al. prepared their sICAM-1 protein in a buffer containing 50 mM triethanolamine (TEA)/20 mM Tris. When this buffer alone was added to control infections (1/10th volume, final concentration 5 mM TEA/2 mM Tris) of HRV3 and HRV14, virtually complete inhibition of CPE was observed. Thus, it is possible that there could be buffer effects on virus replication unrelated to the presence of any form of ICAM.

EXAMPLE 11

Use of Multimeric Forms of tmICAM and tICAMs as Effective Inhibitors of ICAM/LFA-1 Interaction The normal function of ICAM-1 is to serve as a ligand of the leukocyte integrin LFA-1; interaction between these two molecules leads to adhesion between leukocytes and a variety of other cells. The ability of tICAMs to inhibit adhesion between ICAM-1 and LFA-1 on cells was examined as follows. ICAM-1 was adsorbed to microtiter plates as described in Example 7C. JY cells, which express LFA-1, adhere to ICAM-expressing cells or to ICAM-1-coated culture dishes (Staunton, et al., JCB). JY cells ($10^7$ cell/ml in 10 mM HEPES pH 7.5/150 mM NaCl/1 mM $CaCl_2$/1 mM $MgCl_2$ containing 1 mg/ml BSA) labeled with 10 µCi/ml [$^{35}$S]-cysteine for 18 hours) were pre-incubated in the presence or absence of tICAM(453) or tICAM(185) for 30 min at 37 C, and then added to the ICAM-1-coated plates and incubated for 60 min at 37 C. The microtiter plates were then washed three times with media, and the number of cells bound to the plates were quantified by scintillation counting.

As shown in Table 5, tICAM(185) and tICAM(453) both inhibited JY cell binding at identical concentrations of between 5 and 20 µM.

TABLE 5

| µM ICAM-1 | % JY Cell Binding | |
|---|---|---|
| | tICAM(453) | tICAM(185) |
| 20 | 100 | 100 |
| 6 | 5 | 5 |
| 2 | 47 | 50 |
| 0.6 | 83 | 72 |
| 0.02 | 86 | 80 |
| 0.006 | 89 | 97 |

*Binding to ICAM-1-coated microtiter plates; 10 µg/ml anti-LFA-1 or anti-ICAM-1 MAb inhibited binding to <1%.

EXAMPLE 12

Construction of a tICAM(185)/IgG Immunoadhesin

A soluble derivative of ICAM-1 was constructed by a cDNA fusion which linked the first two domains of ICAM-1 (residues 1–185) to a segment of human immunoglobulin heavy chain cDNA. This approach has been described previously for the CD4 molecule [Zettlmeissl, G., J. P. Gregersen, J. M. Duport, S. Mehdi, G. Reiner, and B. Seed, "Expression and Characterization of Human CD4: Immunoglobulin Fusion Proteins", DNA and Cell Biology (1990) 9(5):347–353; Capon, D. J., S. M. Chamow, J. Mordenti, S. A. Marsters, T. Gregory, M. Mitsuya, R. A. Bryn, C. Lucas, F. M. Wurm, J. E. Groopman, S. Broder, and D. H. Smith, "Designing CD4 immunoadhesins for AIDS therapy", Nature (1989) 337:525–531; Traunecker, A. J. Schneider, H. Kiefer and K. Karjalainen, "Highly efficient neutralization of HIV with recombinant CD4-immunoglobulin molecules", Nature (1989) 339:68–70] and resulted in the expression of disulfide-linked dimers.

The cDNA fusion was accomplished by a two-stage polymerase chain reaction (PCR) strategy. [See, e.g., Horton, R. M., Z. Cai, S. N. Ho, and L. R. Pease, "Gene Splicing by Overlap Extension: Tailor-Made Genes Using the Polymerase Chain Reaction", BioTechniques (1990) 8(5):528–535]. The first step involved the separate amplification of a fragment coding for residues 1–185 of ICAM-1 and an IgG heavy chain fragment beginning at residue 216 in the hinge region and ending at the C-terminus of the molecule (see FIG. 3). The PCR primer used at the 3' end of the ICAM-1 fragment contained an additional 24 bases complementary to the first 24 bases of the IgG fragment: CGG TGG GCA TGT GTG AGT TTT GTC AAA GGT CTG GAG CTG GTA GGG GGC. The 5' ICAM-1 primer (5' noncoding and signal sequence) had the sequence:

HindIII
GGA ATT CAA GCT TCT CAG CCT CGC TAT GGC TCC CAG CAG CCC CCG GCC C

The 5' IgG primer had the following sequence: GAC AAA ACT CAC ACA TGC CCA CGG; the 3' primer from the end of the IgG coding sequence was:

<u>XbaI</u>
G GGA TTC TCT AGA TCA TTT ACC CGG AGA CAG GGA GAG GCT

Amplifications were performed using 10 ng of cloned ICAM-1 or IgG1 heavy chain cDNA for 10 cycles with 1 min at 94 C, 2 min at 55 C and 1.5 min extensions at 72 C. The resulting amplified fragments were mixed in approximately equimolar amounts and used as template for the second step PCR reaction. This reaction used the 5' ICAM primer and the 3' IgG primer above. Amplification for 25 cycles under the same conditions as in the first step produced a predominant band of approximately 1200 bp consistent with the desired product (see FIG. 3). The fragment was digested with HindIII and XbaI (restriction sites incorporated into the 5' and 3' primers respectively), purified and ligated into HindIII/XbaI-cleaved CDM8 vector.

Clones containing the desired insert were identified by restriction analysis and two clones designated pHRR72 and pHRR73 were selected for sequence analysis. Sequencing of the junction region between ICAM-1 and the IgG hinge confirmed that both clones had the correct structure. The plasmids were transfected into COS cells which were labelled with [$^{35}$S]cysteine overnight at 48 hours post-transfection as in Example 6. The supernatants were immunoprecipitated with anti-ICAM-1 monoclonal antibody c78.4A and analyzed by SDS gel electrophoresis as in Example 6. Under reducing conditions a band with an apparent molecular weight of 68 kD was specifically immunoprecipitated, corresponding to the ICAM-1/IgG fusion. Expression of clone pHRR72 was consistently higher than pHRR73 so this clone was selected for further study.

COS cells were transfected with pHRR72 according to the method of Example 3 and at 48 hours after transfection the media was replaced with serum-free media containing [$^{35}$S] cysteine and the cells were labelled overnight as above. The supernatants were incubated with protein A-Sepharose beads, and bound protein was eluted with 0.1M acetic acid, neutralized and analyzed by gel electrophoresis under reducing and non-reducing conditions. A control was performed in which plasmids expressing heavy and light chains of a functional antibody were co-transfected. This experiment showed that the protein produced by pHRR72 is capable of binding protein A, showing that the pHRR72 protein contains the IgG constant region, and that the 68 kD and seen under reducing conditions shifts to a high molecular weight dimeric form under non-reducing conditions. Thus since only dimeric IgG binds protein A, and since the mobility under non-reducing conditions is at least twice that of the monomer, we conclude that the tICAM(185)/IgG immunoadhesin is a dimer. Correct folding of the ICAM-1 region is indicated by the specific immunoprecipitation with c78.4A as in Example 6, and by the quantitative detection of the fusion protein using two ICAM-1-specific antibodies in a radioimmune assay (RIA) as in Example 4.

pHRR72 was co-transfected with pSV2-DHFR into CHO cells by the calcium phosphate method of Example 4 and DHFR+ cells were selected in nucleoside-free medium. Individual colonies were picked, expanded and tested by RIA for expression. The three highest-expressing colonies were selected for further study and were recloned by limiting dilution. Analysis of labelled cell supernatants by protein A binding and gel electrophoresis confirmed the expression of tICAM(185)/IgG dimers.

EXAMPLE 13

Efficient Rhinovirus Binding and Neutralization by an tICAM(185)/IgG Immunoadhesin The tICAM(185)/IgG immunoadhesin of Example 12 consists of residues 1–185 of ICAM-1 fused to residue 216 in the hinge region of an IgG1 heavy chain. The molecule is a disulfide-linked dimer containing two rhinovirus binding sites. A CHO cell line CHO72.2 secreting the immunoadhesin was grown overnight in serum-free media containing [$^{35}$S]cysteine and the fusion protein was purified on protein A beads. The labelled protein was tested for rhinovirus binding in the pelleting assay as described in Example 7(A). The samples consisted of tICAM(185)/IgG (no virus), tICAM(185)/IgG+HRV3, tICAM(185)/IgG+HRV3+ c78.4A, and tICAM(185)/IgG+HRV3+irrelevant antibody. Pelleting of labelled protein indicative of virus binding was seen with virus and virus+irrelevant antibody by analysis on SDS gels. No pelleting was seen in the absence of virus and significantly reduced pelleting was seen in the sample containing c78.4A. This result indicates that the tICAM(185)/ IgG binds rhinovirus with a significantly higher affinity than the soluble monomers tICAM(185) and tICAM(453), which do not show levels of binding readily detectable under these conditions. See Example 7(A). While approximately 10% of tmICAM-1 pellets under these conditions, only 1% of tICAM(453) pellets, presumably because tmICAM-1 is in a dimeric state. The result with tICAM(185)/IgG is similar to that seen in this assay with tmICAM-1, suggesting that the two forms of ICAM may have similar affinities for the virus, and providing further evidence that tmICAM-1 is a dimer.

Cell supernatants from CHO72.2 cells containing unpurified tICAM(185)/IgG was tested for rhinovirus neutralization in a virus infectivity assay according to the method of Example 10(B). Serial dilutions of HRV3 were made in media containing 50% IgG supernatant or control supernatant from untransfected CHO cells. The virus dilutions were mixed with HeLa cells and plated in wells of a 96-well microtiter plate (10 wells per dilution). Virus titers were determined by scoring the number of infected wells at each dilution after 6 days. In addition a quantitative assessment of cytopathic effect at high virus input was made 2 days after infection. In experiment A the concentration of tICAM(185)/IgG estimated by RIA was 150 ng/ml and in experiment (B) the concentration was 325 ng/ml.

TABLE 6

| | Experiment A | Experiment B |
|---|---|---|
| HRV3 | 1 × 10$^7$ PFU/ml | 4 × 10$^6$ PFU/ml |
| HRV3 + tICAM(185)/IgG | 6 × 10$^5$ PFU/ml | 5 × 10$^5$ PFU/ml |

Both experiments resulted in a ten-fold reduction in viral titer at a concentration of approximately 1 nM in experiment A and 2 nM in experiment B. For comparison, monomeric tICAM(453) in the same assay results in a 50% reduction in titer at 0.38 µM or 30 µg/ml. Thus the increase in activity resulting from dimerization of the rhinovirus binding site is at least 200-fold and probably greater.

Cell supernatant from CHO72.2 at a concentration of 650 ng/ml (4 nM) was also tested in a competitive binding assay measuring the binding of [$^{35}$S]HRV3 to ICAM-1-coated plastic microtiter wells. Specific binding is determined by comparing counts bound with or without pre-incubation of the ICAM-1 in the well with Mab c78.4A.

TABLE 7

|  | cpm bound* | % binding |
|---|---|---|
| HRV3 | 4945 +/− 58 | 100 |
| HRV3 + CHO supernatant | 5358 +/− 51 | 108 |
| HRV3 + CHO72.2 supernatant | 3187 +/− 206 | 64 |

*Mean values determined from triplicate wells. Standard errors were less than 10% of the mean.

The level of binding in the presence of tICAM(185)/IgG was 65% of the normal control binding and 54% of control binding in the presence of CHO cell supernatant, indicating close to a 50% inhibition of binding. For comparison, soluble monomeric tICAM(453) inhibits HRV3 binding by 50% in the same assay at 240 ug/ml or 3.1 uM. On a molar basis the ICAM-1 IgG immunoadhesin is thus almost a 1000-fold better competitor than the monomer.

EXAMPLE 14

In Vitro Dimerization of ICAM-1

Several lines of evidence indicate that tmICAM-1 exists as a noncovalent dimer at the cell surface: (i) the stoichiometry of HRV/ICAM-1 binding sites at the cell surface is approximately 2; (ii) tICAM(453), despite being properly folded, has a approximately 100-fold lower affinity for HRV than purified tmICAM-1; and (iii) tICAM(453) and tmICAM-1 absorbed to nitrocellulose filters at a high density bind rhinovirus at equivalent levels. See Example 7. In addition, Staunton et al. (Cell 61:243–254 (1990)) have reported that some mutants of ICAM-1 form covalent dimers at the cell surface, indicating that this protein has the capability to self-associate in vivo. Attempts to directly demonstrate the existence of dimers by chemical crosslinking with water-soluble carbodiimide/NHS, which is a heterobifunctional crosslinker which forms a covalent bond between a primary amine and a carboxyl group, did result in crosslinking of tICAM(453) into a 180 kD species, whose size is consistent with a dimer (FIG. 4A). This crosslinking is directly dependent upon the concentration of tICAM (453), with 50% crosslinking at 7 μM protein (FIG. 4B). This concentration is consistent with the relatively high concentration of tmICAM-1 at the surface of a HeLa cell, which is approximately 2.5 μM or 135 μg/ml. The self-association detected by this crosslinking is specific, since it is not affected by high concentrations of third-party proteins (FIG. 4C). tICAM(185) appears to be poorly crosslinked under the same conditions, indicating that domains 3–5 are involved in self-association. Because of the extensive modification of the protein by this crosslinking procedure, the protein had no virus-binding activity. However, this data shows that soluble ICAM can self-associate in solution, and that this self-association is concentration-dependent and -specific.

EXAMPLE 15

A tICAM(1–451)/LFA-3(210–237) Chimera

In order to examine the role of the transmembrane and cytoplasmic domains of tmICAM-1 in high-affinity rhinovirus binding, we constructed a chimeric ICAM-1 which is anchored on the cell surface by a phospholipid tail and lacks these domains (see FIG. 5). This experiment was designed to test whether the cytoplasmic and transmembrane domains are necessary for the formation of dimeric ICAM-1 on the cell surface, which results in the high affinity binding of rhinovirus. In order to modify the ICAM-1 cDNA to express a phospholipid-anchored form, we first used site-directed mutagenesis to create a unique SacII site at residues 450/451 close to the end of the extracellular region. This allowed the isolation of a cDNA fragment coding for residues 1–451 of ICAM-1, by digestion of the modified plasmid with HindIII and SacII. We used PCR to generate a fragment coding for the C-terminal 28 amino acids of the phospholipid-anchored form of LFA-3 (Seed, B., Nature (1987) 329:840–842). By including a SacII site in the 5' primer this fragment was ligated to the ICAM-1 extracellular domain and cloned into the expression vector CDM8, resulting in the plasmid pHRR 70–19. This plasmid contains a cDNA coding for residues 1–451 of ICAM-1 fused to residues 210–237 of LFA-1, which should result in the expression of a phospholipid-anchored molecule containing the ICAM-1 extracellular region. See FIG. 5.

Transfection of COS cells with pHRR 70–19 according to the method of Example 4 and FACS analysis with anti-ICAM-1 antibodies confirmed the cell surface expression of the fusion protein. The binding of [$^{35}$S]-labelled cells to COS cells transfected with the fusion protein was determined.

TABLE 8

| ICAM-1 | cpm bound | % virus input | % control |
|---|---|---|---|
| tmICAM-1 | 2130 +/− 278 | 9.4 | 100 |
| tICAM(1–185)/ LFA-3(210–237) chimera | 2382 +/− 293 | 11.2 | 119 |

This result shows that there is no significant difference between the ability of tmICAM-1 and the tICAM(1–451)/LFA-3(210–237) chimera to bind HRV. It can therefore be concluded that the transmembrane and cytoplasmic domains are not required for HRV binding, and that dimerization must depend on interactions between extracellular regions of the molecule.

Additional evidence that a form of ICAM-1 lacking the cytoplasmic and transmembrane domains functions efficiently as a receptor for rhinoviruses was obtained by transfection of the tICAM(1–451)/LFA-3(210–237) chimeric gene into HeLa 229 cells. We have determined that these cells do not express ICAM-1 on the surface and are resistant to HRV infection. Transfection of either tmICAM-1 or the tICAM(1–451)/LFA-3(210–237) chimera results in cells which are readily infectable with rhinovirus and produce virus at levels comparable to normal HeLa cells.

EXAMPLE 16

Irreversible Inactivation of HRV by ICAM

Figures 6C, 6D:
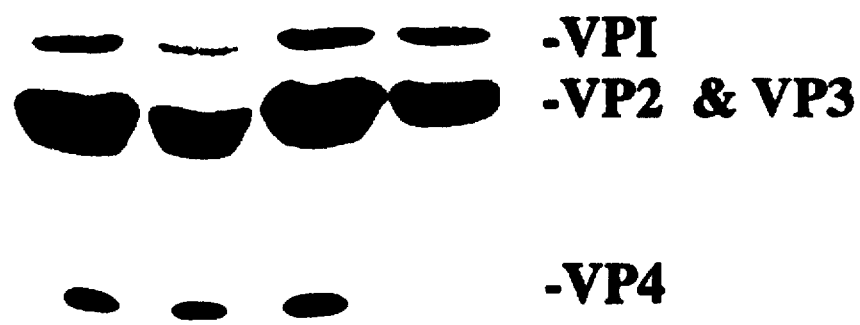
FIG. 6c) SDS-PAGE of [$^{35}$S]methionine-labelled HRV-3 showing loss of VP4.
FIG. 6d) dot-blot hybridization of RNA recovered from HRV3 species with an oligonucleotide probe for HRV. 50 ng of purified HRV3 RNA and RNA extracted from 8 ng of HRV3 species were applied to the blot.

We have demonstrated that tICAM(453) can, in addition to blocking the binding of HRV to cells, irreversibly inactivate HRV. Incubation of HRV with tICAM(453) at 34 C results in conversion of a fraction of the virus from the native 148S form to a 42S form (FIGS. 6A and 6B). The 42S form is non-infectious, lacks the viral subunit VP4, and lacks the RNA genome (empty capsid). This can be shown by SDS-PAGE analysis of [$^{35}$S]methionine-labelled viral particles and by quantitation of viral RNA content by hybridization with a [$^{32}$P]oligonucleotide probe for rhinovirus (5'-GCATTCAGGGGCCGGAG-3') (FIGS. 6C and D). Thus, tICAM(453) can uncoat rhinovirus, an event that normally occurs intracellularly during the course of infection. The uncoating is a slow process, occurring with a t½ of 6 hours at 34 C, in contrast with the inhibition of binding, which occurs with a t½ of <30 minutes. The uncoating is highly temperature-dependent, occurring 10 times faster at 37 C than at 34 C, the optimal temperature of rhinovirus growth. Enhancement of this uncoating activity by soluble forms of ICAM-1 including multimeric configurations of ICAM-1 will lead to improvement of antiviral activity by making neutralization irreversible.

EXAMPLE 17

Cysteine Muteins

To identify the correct site to place cysteine residues for multimerization of ICAM-1, the region of the protein surface involved in self-association must be identified. Domains IV and V have been chosen because they are distal to the viral binding site (domain I) and because domains III-V are implicated in self-association (see Example 14). Since the structure of ICAM-1 is not certain, we have attempted to align the sequence of domains IV and V at the C-terminus of the extracellular domain of ICAM-1 onto the immunoglobulin fold, as ICAM-1 has homology to members of the immunoglobulin supergene family. This alignment is shown diagrammatically in FIG. 7. Then, to identify probable sites involved in self-association, we have examined the three-dimensional structures of several members of the immunoglobulin supergene family, IgG and MHC1/beta-2 microglobulin. Immunoglobulin domains have two broad faces of beta sheet structure, here designated the "B" face and the "F" face. Inspection of the above structures revealed that different immunoglobulin-like domains interacted via one or the other of these faces of the domain. IgG variable regions associated via their F face, while IgG constant regions (CH1, CH2, and CH3) and MHC1/beta-2 microglobulin all interact via their B faces.

ICAM-1 domains have highest homology to constant region-like domains. Thus, the most likely sites of interaction are on the B face of the domains; the most likely sites on the B face to place cysteine residues are close to the center of the B face (adjacent to the cysteine on the B strand that forms the intrachain disulfide bond), where IgG CH3 domains self-associate, or on the N-terminal end of the B face, where IgG CH2 domains and MHC1/beta-2 microglobulin self-associate.

A number of mutants were prepared to identify appropriate sites of interaction. These mutants were prepared by standard site-directed mutagenesis methodology to mutate selected residues to cysteine on tICAM(453) and tmICAM. These cDNAs in the vector CDM8 were then transfected into COS cells and dimer formation accessed by biosynthetic labelling of ICAM-1 with [$^{35}$S]cysteine followed by immunoprecipitation and non-reducing SDS-PAGE analysis. As shown in Table 9, of 13 mutants tested, two have been found to form dimers at a small (about 5%) but significant level:

TABLE 9

| Position of Cysteine | Dimer Formation |
|---|---|
| (tmICAM-1) | |
| 304 | − |
| 306 | − |
| 307 | + |
| 309 | + |
| 375 | − |
| 377 | − |
| 378 | − |
| 380 | − |
| 382 | − |
| 429 | − |
| (tICAM(453)) | |
| 338 | − |
| 360 | − |
| 378 | − |

These two muteins, Cys-307 and Cys-309, are both located on the N-terminal end of the B face of domain IV. The relatively low level of dimerization may reflect the low concentration of ICAM-1 on the cell surface (low expression), or imperfect orientation of the cysteine residues relative to the site of interaction. These data indicate that this region of the domain is a likely site of interaction. Other residues adjacent to residues 307 and 309, e.g. His-308, Arg-310, Glu-294, Arg-326, Gln-328, are likely to increase the efficiency of the dimer formation. Mutations that lead to dimer formation of tmICAM-1 will then be placed on tICAM(453) for the secretion of soluble ICAM-1 dimers.

The foregoing examples describe the creation of soluble, multimeric forms of tICAM that substantially increase tICAM binding and neutralizing activity.

While the present invention has been described in terms of specific methods and compositions, it is understood that variations and modifications will occur to those skilled in the art upon consideration of the present invention.

For example, it is anticipated that smaller protein fragments and peptides derived from ICAM-1 that still contain the virus-binding site would also be effective in a multimeric configuration. It is also anticipated that multimeric ICAM may be effective inhibitors of the ICAM-1/LFA-1 interaction, as the affinity between these two molecules is quite low and the cell-cell binding mediated by these two molecules is highly cooperative.

Although the preferred form and configuration is a non-transmembrane (truncated) ICAM in dimeric configuration, it is not intended to preclude other forms and configurations effective in binding virus and effective in neutralizing viral activity from being included in the scope of the present invention.

Further, it is anticipated that the general method of the invention of preparing soluble protein forms from insoluble, normally membrane bound receptor proteins can be used to prepare soluble multimeric forms of other receptor proteins useful for binding to and decreasing infectivity of viruses other than those that bind to the "major group" receptor. Such other viruses include polio, Herpes simplex, and Epstein-Barr virus.

Numerous modifications and variations in the invention as described in the above illustrative examples are expected to occur to those skilled in the art and consequently only such limitations as appear in the appended claims should be placed thereon.

Accordingly it is intended in the appended claims to cover all such equivalent variations which come within the scope of the invention as claimed.

What is claimed is:

1. A multimeric antiviral agent comprising two units wherein said units may be the same or different and are each independently selected from the group consisting of transmembrane intercellular adhesion molecule-1 (tmICAM-1) and truncated forms of intercellular adhesion molecule-1 (tICAMs), each of said units containing at least one unpaired cysteine residue at a position selected from the group consisting of 307 and 309, wherein each of said units is linked to at least one other of said units via a disulfide bridge, and wherein said multimeric antiviral agent binds to HRV and reduces infectivity thereof.

2. A multimeric antiviral agent according to claim 1 wherein said tICAM is selected from the group consisting of tICAM(453) and tICAM(185).

3. The multimeric antiviral agent of claim 1 which is dimeric tmICAM-1 wherein each monomer of tmICAM-1 contains a cysteine residue at position 307 and said cysteine residues form a disulfide bridge.

4. The multimeric antiviral agent of claim 1 which is dimeric tmICAM-1 wherein each monomer of tmICAM-1 contains a cysteine residue at position 309 and said cysteine residues form a disulfide bridge.

5. The multimeric antiviral agent of claim 1 which is dimeric tICAM(453) wherein each monomer of tICAM (453) contains a cysteine residue at position 307 and said cysteine residues form a disulfide bridge.

6. The multimeric antiviral agent of claim 1 which is dimeric tICAM(453) wherein each monomer of tICAM (453) contains a cysteine residue at position 309 and said cysteine residues form a disulfide bridge.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: synthetic oligonucleotide ( i i i ) HYPOTHETICAL: No ( i v ) ANTI-SENSE: No ( i x ) FEATURE:
        ( A ) NAME/KEY: G
        ( B ) LOCATION: 5'terminus
        ( D ) OTHER INFORMATION: extra base at 5'terminus
        ( A ) NAME/KEY: EcoRI site
        ( B ) LOCATION: bases 2-7
        ( A ) NAME/KEY: 24 bases coding for the first 8
            amino acid residues of human ICAM-1
        ( B ) LOCATION: bases 8-31

( x ) PUBLICATION INFORMATION:
        ( A ) AUTHORS: Staunton, D.
            Marlin, S.
            Stratowa, C.
            Dustin, M.
            Springer, T.
        ( B ) TITLE: Primary Structure of ICAM-1 demonstrates
            interaction between members of the immunoglobulin
            and integrin supergene families
        ( C ) JOURNAL: Cell
        ( D ) VOLUME: 52
        ( F ) PAGES: 925-933
        ( G ) DATE: 25-MAR-1988
        ( K ) RELEVANT RESIDUES IN SEQ ID NO:1: from 8 to 31

( x i ) SEQUENCE DESCRIPTION: SEQ ID NO:1:

```
GGAATTC ATG GCT CCC AGC AGC CCC CGG CCC                     31
        Met Ala Pro Ser Ser Pro Arg Pro
                         5
```

( 2 ) INFORMATION FOR SEQ ID NO:2:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( i i ) MOLECULE TYPE: synthetic oligonucleotide ( i i i ) HYPOTHETICAL: No ( i v ) ANTI-SENSE: Yes ( i x ) FEATURE:
        ( A ) NAME/KEY: G
        ( B ) LOCATION: 5'terminus
        ( D ) OTHER INFORMATION: extra base at 5'terminus
        ( A ) NAME/KEY: EcoRI site
        ( B ) LOCATION: bases 2-7
        ( A ) NAME/KEY: 24 bases complementary to the sequence
            coding for the last 8 amino acid residues of human
            ICAM-1
        ( B ) LOCATION: bases 8-31

( x ) PUBLICATION INFORMATION:

(A) AUTHORS: Staunton, D.
Marlin, S.
Stratowa, C.
Dustin, M.
Springer, T.
(B) TITLE: Primary Structure of ICAM-1 demonstrates
interaction between members of the immunoglobulin
and integrin supergene families
(C) JOURNAL: Cell
(D) VOLUME: 52
(F) PAGES: 925-933
(G) DATE: 25-MAR-1988
(K) RELEVANT RESIDUES IN SEQ ID NO:2: from 8 to 31

(xi) SEQUENCE DESCRIPTION: SEQ ID NO:2:

GGAATTCTCA GGGAGGCGTG GCTTGTGTGT T 31

(2) INFORMATION FOR SEQ ID NO:3:

(i) SEQUENCE CHARACTERISTICS:
(A) LENGTH: 47
(B) TYPE: nucleic acid
(C) STRANDEDNESS: single
(D) TOPOLOGY: linear (ii) MOLECULE TYPE: synthetic oligonucleotide (iii) HYPOTHETICAL: No (iv) ANTI-SENSE: Yes (ix) FEATURE:
(A) NAME/KEY: 47 bases complementary to bases 622-668
of human ICAM-1 sequence (corresponding to amino
acid residues 162-177)
(B) LOCATION: bases 1-47

(x) PUBLICATION INFORMATION:
(A) AUTHORS: Staunton, D.
Marlin, S.
Stratowa, C.
Dustin, M.
Springer, T.
(B) TITLE: Primary Structure of ICAM-1
demonstrates interaction between members of the
immunoglobulin and integrin supergene families
(C) JOURNAL: Cell
(D) VOLUME: 52
(F) PAGES: 925-933
(G) DATE: 25-MAR-1988
(K) RELEVANT RESIDUES IN SEQ ID NO:3: from 1 to 47

(xi) SEQUENCE DESCRIPTION: SEQ ID NO:3:

GAGGTGTTCT CAAACAGCTC CAGCCCTTGG GGCCGCAGGT CCAGTTC 47

(2) INFORMATION FOR SEQ ID NO:4:

(i) SEQUENCE CHARACTERISTICS:
(A) LENGTH: 47
(B) TYPE: nucleic
(C) STRANDEDNESS: single
(D) TOPOLOGY: linear (ii) MOLECULE TYPE: synthetic oligonucleotide (iii) HYPOTHETICAL: No (iv) ANTI-SENSE: Yes (ix) FEATURE:
(A) NAME/KEY: 47 bases complementary to bases 659-705
of human ICAM-1 sequence (corresponding to amino
acid residues 1-17)
(B) LOCATION: bases 1-47

(x) PUBLICATION INFORMATION:

(A) AUTHORS: Staunton, D.
   Marlin, S.
   Stratowa, C.
   Dustin, M.
   Springer, T.
(B) TITLE: Primary Structure of ICAM-1 demonstrates
   interaction between members of the immunoglobulin
   and integrin supergene families
(C) JOURNAL: Cell
(D) VOLUME: 52
(F) PAGES: 925-933
(G) DATE: 25-MAR-1988
(K) RELEVANT RESIDUES IN SEQ ID NO:4: from 1 to 47

(xi) SEQUENCE DESCRIPTION: SEQ ID NO:4:

CGCTGGCAGG ACAAAGGTCT GGAGCTGGTA GGGGGCCGAG GTGTTCT                       47

(2) INFORMATION FOR SEQ ID NO:5:

(i) SEQUENCE CHARACTERISTICS:
      (A) LENGTH: 49
      (B) TYPE: nucleic
      (C) STRANDEDNESS: single
      (D) TOPOLOGY: linear (ii) MOLECULE TYPE: synthetic oligonucleotide (iii) HYPOTHETICAL: No (iv) ANTI-SENSE: No (ix) FEATURE:
      (A) NAME/KEY: G
      (B) LOCATION: 5'terminus
      (D) OTHER INFORMATION: extra base at 5'terminus
      (A) NAME/KEY: EcoRI site
      (B) LOCATION: bases 2-7
      (A) NAME/KEY: HindIII site
      (B) LOCATION: bases 8-13
      (A) NAME/KEY: human ICAM-1 5'untranslated region
      (B) LOCATION: bases 14-25
      (A) NAME/KEY: human ICAM-1 sequence coding for the
          first 8 amino acid residues
      (B) LOCATION: bases 26-49

(x) PUBLICATION INFORMATION:
      (A) AUTHORS: Staunton, D.
         Marlin, S.
         Stratowa, C.
         Dustin, M.
         Springer, T.
      (B) TITLE: Primary Structure of ICAM-1 demonstrates
         interaction between members of the immunoglobulin
         and integrin supergene families
      (C) JOURNAL: Cell
      (D) VOLUME: 52
      (F) PAGES: 925-933
      (G) DATE: 25-MAR-1988
      (K) RELEVANT RESIDUES IN SEQ ID NO:5: from 14 to 49

(xi) SEQUENCE DESCRIPTION: SEQ ID NO:5:

GGAATTCAAG CTTCTCAGCC TCGCT ATG GCT CCC AGC AGC CCC CGG CCC            49
                           Met Ala Pro Ser Ser Pro Arg Pro
                                       5

(2) INFORMATION FOR SEQ ID NO:6:

(i) SEQUENCE CHARACTERISTICS:
      (A) LENGTH: 40
      (B) TYPE: nucleic
      (C) STRANDEDNESS: single
      (D) TOPOLOGY: linear (ii) MOLECULE TYPE: synthetic oligonucleotide (iii) HYPOTHETICAL: No (iv) ANTI-SENSE: Yes (ix) FEATURE:
    (A) NAME/KEY: G
    (B) LOCATION: 5'terminus
    (D) OTHER INFORMATION: extra base at 5'terminus
    (A) NAME/KEY: EcoRI site
    (B) LOCATION: bases 2-7
    (A) NAME/KEY: PstI site
    (B) LOCATION: bases 8-13
    (A) NAME/KEY: stop codon
    (B) LOCATION: bases 14-16
    (A) NAME/KEY: 24 bases complementary to sequence coding
        for amino acid residues 446-453 of human ICAM-1
    (B) LOCATION: bases 17-40

(x) PUBLICATION INFORMATION:
    (A) AUTHORS: Staunton, D.
        Marlin, S.
        Stratowa, C.
        Dustin, M.
        Springer, T.
    (B) TITLE: Primary Structure of ICAM-1 demonstrates
        interaction between members of the immunoglobulin
        and integrin supergene families
    (C) JOURNAL: Cell
    (D) VOLUME: 52
    (F) PAGES: 925-933
    (G) DATE: 25-MAR-1988
    (K) RELEVANT RESIDUES IN SEQ ID NO:6: from 17 to 40

(xi) SEQUENCE DESCRIPTION: SEQ ID NO:6:

GGAATTCCTG CAGTCACTCA TACCGGGGGG AGAGCACATT     40

(2) INFORMATION FOR SEQ ID NO:7:

(i) SEQUENCE CHARACTERISTICS:
        (A) LENGTH: 40
        (B) TYPE: nucleic
        (C) STRANDEDNESS: single
        (D) TOPOLOGY: linear (ii) MOLECULE TYPE: synthetic oligonucleotide (iii) HYPOTHETICAL: No (iv) ANTI-SENSE: Yes (ix) FEATURE:
        (A) NAME/KEY: T
        (B) LOCATION: 5'terminus
        (D) OTHER INFORMATION: extra base at 5'terminus
        (A) NAME/KEY: XbaI site
        (B) LOCATION: bases 2-7
        (A) NAME/KEY: BamHI site
        (B) LOCATION: bases 8-13
        (A) NAME/KEY: stop codon
        (B) LOCATION: bases 14-16
        (A) NAME/KEY: sequence complementary to bases 670-693
            of human ICAM-1 (corresponding to amino acid
            residues 178-185)
        (B) LOCATION: bases 17-40

(x) PUBLICATION INFORMATION:
        (A) AUTHORS: Staunton, D.
            Marlin, S.
            Stratowa, C.
            Dustin, M.
            Springer, T.
        (B) TITLE: Primary Structure of ICAM-1 demonstrates
            interaction between members of the immunoglobulin
            and integrin supergene families
        (C) JOURNAL: Cell
        (D) VOLUME: 52
        (F) PAGES: 925-933
        (G) DATE: 25-MAR-1988
        (K) RELEVANT RESIDUES IN SEQ ID NO:7: from 17 to 40

( x i ) SEQUENCE DESCRIPTION: SEQ ID NO:7:

TTCTAGAGGA TCCTCAAAAG GTCTGGAGCT GGTAGGGGGC					40

( 2 ) INFORMATION FOR SEQ ID NO:8:

( i ) SEQUENCE CHARACTERISTICS:
        ( A ) LENGTH: 43
        ( B ) TYPE: nucleic
        ( C ) STRANDEDNESS: single
        ( D ) TOPOLOGY: linear ( i i ) MOLECULE TYPE: synthetic oligonucleotide ( i i i ) HYPOTHETICAL: No ( i v ) ANTI-SENSE: Yes ( x ) FEATURE:
        ( A ) NAME/KEY: T
        ( B ) LOCATION: 5'terminus
        ( D ) OTHER INFORMATION: extra base at 5'terminus
        ( A ) NAME/KEY: XbaI site
        ( B ) LOCATION: bases 2-7
        ( A ) NAME/KEY: BamHI site
        ( B ) LOCATION: bases 8-13
        ( A ) NAME/KEY: stop codon
        ( B ) LOCATION: bases 14-16
        ( A ) NAME/KEY: lysine codon
        ( B ) LOCATION: bases 17-19
        ( A ) NAME/KEY: 24 bases complementary to the sequence
               coding for amino acid residues corresponding to
               residues 446- 453 of human ICAM-1
        ( B ) LOCATION: bases 20-43

( x ) PUBLICATION INFORMATION:
        ( A ) AUTHORS: Staunton, D.
               Marlin, S.
               Stratowa, C.
               Dustin, M.
               Springer, T.
        ( B ) TITLE: Primary Structure of ICAM- 1 demonstrates
               interaction between members of the immunoglobulin
               and integrin supergene families
        ( C ) JOURNAL: Cell
        ( D ) VOLUME: 52
        ( F ) PAGES: 925-933
        ( G ) DATE: 25-MAR-1988
        ( K ) RELEVANT RESIDUES IN SEQ ID NO:8: from 20 to 43

( x i ) SEQUENCE DESCRIPTION: SEQ ID NO:8:

TTCTAGAGGA TCCTCACTTC TCATACCGGG GGGAGAGCAC ATT					43

( 2 ) INFORMATION FOR SEQ ID NO:9:

( i ) SEQUENCE CHARACTERISTICS:
        ( A ) LENGTH: 43
        ( B ) TYPE: nucleic
        ( C ) STRANDEDNESS: single
        ( D ) TOPOLOGY: linear ( i i ) MOLECULE TYPE: synthetic oligonucleotide ( i i i ) HYPOTHETICAL: No ( i v ) ANTI-SENSE: Yes ( i x ) FEATURE:
        ( A ) NAME/KEY: T
        ( B ) LOCATION: 5'terminus
        ( D ) OTHER INFORMATION: extra base at 5'terminus
        ( A ) NAME/KEY: XbaI site
        ( B ) LOCATION: bases 2-7
        ( A ) NAME/KEY: BamHI site
        ( B ) LOCATION: bases 8-13
        ( A ) NAME/KEY: stop codon (B) LOCATION: bases 14-16
                (A) NAME/KEY: lysine codon
                (B) LOCATION: bases 17-19
                (A) NAME/KEY: 24 bases complementary to the sequence
                        coding for amino acid residues 178-185 of human
                        ICAM-1
                (B) LOCATION: bases 20-43

(x) PUBLICATION INFORMATION:
                (A) AUTHORS: Staunton, D.
                        Marlin, S.
                        Stratowa, C.
                        Dustin, M.
                        Springer, T.
                (B) TITLE: Primary Structure of ICAM-1 demonstrates
                        interaction between members of the immunoglobulin
                        and integrin supergene families
                (C) JOURNAL: Cell
                (D) VOLUME: 52
                (F) PAGES: 925-933
                (G) DATE: 25-MAR-1988
                (K) RELEVANT RESIDUES IN SEQ ID NO:9: from 20 to 43

(x i) SEQUENCE DESCRIPTION: SEQ ID NO:9:

TTCTAGAGGA TCCTCACTTA AAGGTCTGGA GCTGGTAGGG GGC                    43

(2) INFORMATION FOR SEQ ID NO:10:

(i) SEQUENCE CHARACTERISTICS:
                (A) LENGTH: 48
                (B) TYPE: nucleic
                (C) STRANDEDNESS: single
                (D) TOPOLOGY: linear (ii) MOLECULE TYPE: synthetic oligonucleotide (iii) HYPOTHETICAL: No (iv) ANTI-SENSE: Yes (ix) FEATURE:
                (A) NAME/KEY: 24 bases complementary to sequence coding
                        for amino acid residues 216-223 of human IgG1
                        heavy chain
                (B) LOCATION: bases 1-24
                (A) NAME/KEY: 24 bases complementary to sequence coding
                        for amino acid residues 178-185 of human ICAM-1
                (B) LOCATION: bases 25-48

(x) PUBLICATION INFORMATION:
                (A) AUTHORS: Ellison, J.W.
                        Berson, B.J.
                        Hood, L.E.
                (B) TITLE: The nucleotide sequence of a human
                        immunoglobulin C-gamma-1 gene
                (C) JOURNAL: Nucleic Acids Research
                (D) VOLUME: 10
                (F) PAGES: 4071-4079
                (G) DATE: 1982
                (K) RELEVANT RESIDUES IN SEQ ID NO:10: from 1 to 24
                (A) AUTHORS: Staunton, D.
                        Marlin, S.
                        Stratowa, C.
                        Dustin, M.
                        Springer, T.
                (B) TITLE: Primary Structure of ICAM-1 demonstrates
                        interaction between members of the immunoglobulin
                        and integrin supergene families
                (C) JOURNAL: Cell
                (D) VOLUME: 52
                (F) PAGES: 925-933
                (G) DATE: 25-MAR-1988
                (K) RELEVANT RESIDUES IN SEQ ID NO:10: from 25 to 48

(x i) SEQUENCE DESCRIPTION: SEQ ID NO:10:

CGGTGGGCAT GTGTGAGTTT TGTCAAAGGT CTGGAGCTGG TAGGGGGC               48

( 2 ) INFORMATION FOR SEQ ID NO:11:

( i ) SEQUENCE CHARACTERISTICS:
        ( A ) LENGTH: 24
        ( B ) TYPE: nucleic
        ( C ) STRANDEDNESS: single
        ( D ) TOPOLOGY: linear ( i i ) MOLECULE TYPE: synthetic oligonucleotide ( i i i ) HYPOTHETICAL: No ( i v ) ANTI-SENSE: No ( i x ) FEATURE:
        ( A ) NAME/KEY: sequence coding for residues 216-223 of
            human IgG1 heavy chain
        ( B ) LOCATION: bases 1-24

( x ) PUBLICATION INFORMATION:
        ( A ) AUTHORS: Ellison, J.W.
            Berson, B.J.
            Hood, L.E.
        ( B ) TITLE: The nucleotide sequence of a human
            immunoglobulin C-gamma-1 gene
        ( C ) JOURNAL: Nucleic Acids Research
        ( D ) VOLUME: 10
        ( F ) PAGES: 4071-4079
        ( G ) DATE: 1982
        ( K ) RELEVANT RESIDUES IN SEQ ID NO:11: from 1 to 24

( x i ) SEQUENCE DESCRIPTION: SEQ ID NO:11:

```
GAC AAA ACT CAC ACA TGC CCA CGG                                    24
Asp Lys Thr His Thr Ser Pro Arg
                 5
```

( 2 ) INFORMATION FOR SEQ ID NO:12:

( i ) SEQUENCE CHARACTERISTICS:
        ( A ) LENGTH: 40
        ( B ) TYPE: nucleic
        ( C ) STRANDEDNESS: single
        ( D ) TOPOLOGY: linear ( i i ) MOLECULE TYPE: synthetic oligonucleotide ( i i i ) HYPOTHETICAL: No ( i v ) ANTI-SENSE: Yes ( i x ) FEATURE:
        ( A ) NAME/KEY: G
        ( B ) LOCATION: 5'terminus
        ( D ) OTHER INFORMATION: extra base at 5'terminus
        ( A ) NAME/KEY: BamHI site
        ( B ) LOCATION: bases 2-7
        ( A ) NAME/KEY: XbaI site
        ( B ) LOCATION: bases 8-13
        ( A ) NAME/KEY: stop codon
        ( B ) LOCATION: bases 14-16
        ( A ) NAME/KEY: sequence complementary to sequence coding
            for last 8 residues of human IgG1 heavy chain
        ( B ) LOCATION: bases 17-40

( x ) PUBLICATION INFORMATION:
        ( A ) AUTHORS: Ellison, J.W.
            Berson, B.J.
            Hood, L.E.
        ( B ) TITLE: The nucleotide sequence of a human
            immunoglobulin C-gamma-1 gene
        ( C ) JOURNAL: Nucleic Acids Research
        ( D ) VOLUME: 10
        ( F ) PAGES: 4071-4079
        ( G ) DATE: 1982
        ( K ) RELEVANT RESIDUES IN SEQ ID NO:12: from 14 to 40

( x i ) SEQUENCE DESCRIPTION: SEQ ID NO:12:

GGGATTCTCT AGATCATTTA CCCGGAGACA GGGAGAGGCT    40

( 2 ) INFORMATION FOR SEQ ID NO:13:

( i ) SEQUENCE CHARACTERISTICS:
        ( A ) LENGTH: 17
        ( B ) TYPE: nucleic
        ( C ) STRANDEDNESS: single
        ( D ) TOPOLOGY: linear ( i i ) MOLECULE TYPE: synthetic oligonucleotide ( i i i ) HYPOTHETICAL: No ( i v ) ANTI-SENSE: Yes ( i x ) FEATURE:
        ( A ) NAME/KEY: sequence complimentary to bases 471-455
            of HRV 14
        ( B ) LOCATION: bases 1-17

( x ) PUBLICATION INFORMATION:
        ( A ) AUTHORS: Stanway, G.
            Hughes, P.J.
            Mountford, R.C.
            Minor, P.D.
            Almond, J.W.
        ( B ) TITLE: The complete nucleotide sequence of a common
            cold virus: human rhinovirus 14
        ( C ) JOURNAL: Nucleic Acids Research
        ( D ) VOLUME: 12
        ( F ) PAGES: 7859
        ( G ) DATE: 1984
        ( K ) RELEVANT RESIDUES IN SEQ ID NO:13: from 1 to 17

( x i ) SEQUENCE DESCRIPTION: SEQ ID NO:13:

GCATTCAGGG GCCGGAG    17

( 2 ) INFORMATION FOR SEQ ID NO:14:

( i ) SEQUENCE CHARACTERISTICS:
        ( A ) LENGTH: 507
        ( B ) TYPE: amino acid
        ( C ) STRANDEDNESS: single
        ( D ) TOPOLOGY: linear ( i i ) MOLECULE TYPE: protein ( i i i ) HYPOTHETICAL: No ( i x ) FEATURE:
        ( A ) NAME/KEY: human ICAM-1
        ( D ) OTHER INFORMATION: Staunton et al. and Simmons et
            al. (see references cited below) differ in their
            numbering schemes for the ICAM-1 molecule.
            Simmons et al. postulate that the mature protein
            is as set forth in SEQ ID NO:14. Staunton et al.
            believe that the mature ICAM-1 protein begins at
            amino acid residue number 3 (Gln) of Simmons et
            al.

( x ) PUBLICATION INFORMATION:
        ( A ) AUTHORS: Simmons, D.
            Makgoba, M.
            Seed, B.
        ( B ) TITLE: ICAM, an adhesion ligand of LFA-1, is
            homologous to the neural cell adhesion molecule
            NCAM
        ( C ) JOURNAL: Nature
        ( D ) VOLUME: 331
        ( F ) PAGES: 624-627
        ( G ) DATE: 18-FEB-1988
        ( K ) RELEVANT RESIDUES IN SEQ ID NO:14: from 1 to 507
        ( A ) AUTHORS: Staunton, D.
            Marlin, S.
            Stratowa, C.

Dustin, M.
Springer, T.
(B) TITLE: Primary Structure of ICAM-1 demonstrates
    interaction between members of the immunoglobulin
    and integrin supergene families
(C) JOURNAL: Cell
(D) VOLUME: 52
(F) PAGES: 925-933
(G) DATE: 25-MAR-1988
(K) RELEVANT RESIDUES IN SEQ ID NO:14: from 3 to 507

(x i) SEQUENCE DESCRIPTION: SEQ ID NO:14:

| | | | | | | | | | | | | | | |
|---|---|---|---|---|---|---|---|---|---|---|---|---|---|---|
| Asn | Ala | Gln | Thr | Ser<br>5 | Val | Ser | Pro | Ser | Lys<br>10 | Val | Ile | Leu | Pro | Arg<br>15 |
| Gly | Gly | Ser | Val | Leu<br>20 | Val | Thr | Cys | Ser | Thr<br>25 | Ser | Cys | Asp | Gln | Pro<br>30 |
| Lys | Leu | Leu | Gly | Ile<br>35 | Glu | Thr | Pro | Leu | Pro<br>40 | Lys | Lys | Glu | Leu | Leu<br>45 |
| Leu | Pro | Gly | Asn | Asn<br>50 | Arg | Lys | Val | Tyr | Glu<br>55 | Leu | Ser | Asn | Val | Gln<br>60 |
| Glu | Asp | Ser | Gln | Pro<br>65 | Met | Cys | Tyr | Ser | Asn<br>70 | Cys | Pro | Asp | Gly | Gln<br>75 |
| Ser | Thr | Ala | Lys | Thr<br>80 | Phe | Leu | Thr | Val | Tyr<br>85 | Trp | Thr | Pro | Glu | Arg<br>90 |
| Val | Glu | Leu | Ala | Pro<br>95 | Leu | Pro | Ser | Trp | Gln<br>100 | Pro | Val | Gly | Lys | Asn<br>105 |
| Leu | Thr | Leu | Arg | Cys<br>110 | Gln | Val | Glu | Gly | Gly<br>115 | Ala | Pro | Arg | Ala | Asn<br>120 |
| Leu | Thr | Val | Val | Leu<br>125 | Leu | Arg | Gly | Glu | Lys<br>130 | Glu | Leu | Lys | Arg | Glu<br>135 |
| Pro | Ala | Val | Gly | Glu<br>140 | Pro | Ala | Glu | Val | Thr<br>145 | Thr | Thr | Val | Leu | Val<br>150 |
| Arg | Arg | Asp | His | His<br>155 | Gly | Ala | Asn | Phe | Ser<br>160 | Cys | Arg | Thr | Glu | Leu<br>165 |
| Asp | Leu | Arg | Pro | Gln<br>170 | Gly | Leu | Glu | Leu | Phe<br>175 | Glu | Asn | Thr | Ser | Ala<br>180 |
| Pro | Tyr | Gln | Leu | Gln<br>185 | Thr | Phe | Val | Leu | Pro<br>190 | Ala | Thr | Pro | Pro | Gln<br>195 |
| Leu | Val | Ser | Pro | Arg<br>200 | Val | Leu | Glu | Val | Asp<br>205 | Thr | Gln | Gly | Thr | Val<br>210 |
| Val | Cys | Ser | Leu | Asp<br>215 | Gly | Leu | Phe | Pro | Val<br>220 | Ser | Glu | Ala | Gln | Val<br>225 |
| His | Leu | Ala | Leu | Gly<br>230 | Asp | Gln | Arg | Leu | Asn<br>235 | Pro | Thr | Val | Thr | Tyr<br>240 |
| Gly | Asn | Asp | Ser | Phe<br>245 | Ser | Ala | Lys | Ala | Ser<br>250 | Val | Ser | Val | Thr | Ala<br>255 |
| Glu | Asp | Glu | Gly | Thr<br>260 | Gln | Arg | Leu | Thr | Cys<br>265 | Ala | Val | Ile | Leu | Gly<br>270 |
| Asn | Gln | Ser | Gln | Glu<br>275 | Thr | Leu | Gln | Thr | Val<br>280 | Thr | Ile | Tyr | Ser | Phe<br>285 |
| Pro | Ala | Pro | Asn | Val<br>290 | Ile | Leu | Thr | Lys | Pro<br>295 | Glu | Val | Ser | Glu | Gly<br>300 |
| Thr | Glu | Val | Thr | Val<br>305 | Lys | Cys | Glu | Ala | His<br>310 | Pro | Arg | Ala | Lys | Val<br>315 |
| Thr | Leu | Asn | Gly | Val<br>320 | Pro | Ala | Gln | Pro | Leu<br>325 | Gly | Pro | Arg | Ala | Gln<br>330 |
| Leu | Leu | Leu | Lys | Ala | Thr | Pro | Glu | Asp | Asn | Gly | Arg | Ser | Phe | Ser |

|   |   |   |   | 335 |   |   |   | 340 |   |   |   | 345 |
|---|---|---|---|---|---|---|---|---|---|---|---|---|
| Cys | Ser | Ala | Thr | Leu | Glu | Val | Ala | Gln | Leu | Ile | His | Lys | Asn |
|   |   |   |   | 350 |   |   |   | 355 |   |   |   | 360 |
| Gln | Thr | Arg | Glu | Leu | Arg | Val | Leu | Tyr | Gly | Pro | Arg | Leu | Asp | Glu |
|   |   |   |   | 365 |   |   |   | 370 |   |   |   | 375 |
| Arg | Asp | Cys | Pro | Gly | Asn | Trp | Thr | Trp | Pro | Glu | Asn | Ser | Gln | Gln |
|   |   |   |   | 380 |   |   |   | 385 |   |   |   | 390 |
| Thr | Pro | Met | Cys | Gln | Ala | Trp | Gly | Asn | Pro | Leu | Pro | Glu | Leu | Lys |
|   |   |   |   | 395 |   |   |   | 400 |   |   |   | 405 |
| Cys | Leu | Lys | Asp | Gly | Thr | Phe | Pro | Leu | Pro | Ile | Gly | Glu | Ser | Val |
|   |   |   |   | 410 |   |   |   | 415 |   |   |   | 420 |
| Thr | Val | Thr | Arg | Asp | Leu | Glu | Gly | Thr | Tyr | Leu | Cys | Arg | Ala | Arg |
|   |   |   |   | 425 |   |   |   | 430 |   |   |   | 435 |
| Ser | Thr | Gln | Gly | Glu | Val | Thr | Arg | Glu | Val | Thr | Val | Asn | Val | Leu |
|   |   |   |   | 440 |   |   |   | 445 |   |   |   | 450 |
| Ser | Pro | Arg | Tyr | Glu | Ile | Val | Ile | Ile | Thr | Val | Val | Ala | Ala | Ala |
|   |   |   |   | 455 |   |   |   | 460 |   |   |   | 465 |
| Val | Ile | Met | Gly | Thr | Ala | Gly | Leu | Ser | Thr | Tyr | Leu | Tyr | Asn | Arg |
|   |   |   |   | 470 |   |   |   | 475 |   |   |   | 480 |
| Gln | Arg | Lys | Ile | Lys | Lys | Tyr | Arg | Leu | Gln | Gln | Ala | Gln | Lys | Gly |
|   |   |   |   | 485 |   |   |   | 490 |   |   |   | 495 |
| Thr | Pro | Met | Lys | Pro | Asn | Thr | Gln | Ala | Thr | Pro | Pro |   |   |   |
|   |   |   |   | 500 |   |   |   | 505 |   |   |   |   |